United States Patent
Reed

(10) Patent No.: US 11,090,097 B2
(45) Date of Patent: Aug. 17, 2021

(54) CONNECTING END EFFECTORS TO SURGICAL DEVICES

(71) Applicant: Covidien LP, Mansfield, MA (US)

(72) Inventor: Scott Reed, Winsted, CT (US)

(73) Assignee: COVIDIEN LP, Mansfield, MA (US)

( * ) Notice: Subject to any disclaimer, the term of this patent is extended or adjusted under 35 U.S.C. 154(b) by 1334 days.

(21) Appl. No.: 15/052,952

(22) Filed: Feb. 25, 2016

(65) Prior Publication Data

US 2016/0270835 A1 Sep. 22, 2016

Related U.S. Application Data

(60) Provisional application No. 62/134,107, filed on Mar. 17, 2015.

(51) Int. Cl.
*A61B 17/88* (2006.01)
*A61B 17/00* (2006.01)
(Continued)

(52) U.S. Cl.
CPC .... *A61B 17/8883* (2013.01); *A61B 17/00234* (2013.01); *A61B 17/068* (2013.01);
(Continued)

(58) Field of Classification Search
CPC .............. A61B 17/068; A61B 17/8872; A61B 2090/038; A61B 2017/00367;
(Continued)

(56) References Cited

U.S. PATENT DOCUMENTS

| | | | |
|---|---|---|---|
| 3,032,359 A | * | 5/1962 | Cator ...................... F16L 37/23 |
| | | | 285/277 |
| 3,866,510 A | | 2/1975 | Eibes et al. |

(Continued)

FOREIGN PATENT DOCUMENTS

| | | |
|---|---|---|
| CA | 2857855 A1 | 2/2015 |
| CN | 2547267 Y | 4/2003 |

(Continued)

OTHER PUBLICATIONS

Extended European Search Report corresponding to counterpart Int'l Appln. No. EP 14 81 7036.8 dated Feb. 2, 2017.

(Continued)

*Primary Examiner* — Nathaniel C Chukwurah
*Assistant Examiner* — Lucas E. A. Palmer
(74) *Attorney, Agent, or Firm* — Carter, DeLuca & Farrell LLP

(57) ABSTRACT

A surgical fastener applying device for releasable connection to an end effector is provided. The surgical fastener applying device includes an elongated body portion having an outer tube and an inner shaft assembly. The inner shaft assembly defines a non-circular bore in a distal end thereof. The inner shaft assembly is longitudinally movable through the outer tube. The outer tube and the inner shaft assembly define corresponding openings extending radially therethrough. The surgical fastener applying device includes a detent movable within the openings of the elongated body portion. The detent floats between the end effector and the elongated body portion to enable selective connection between the end effector and the elongated body portion.

20 Claims, 11 Drawing Sheets

(51) Int. Cl.
    *A61B 17/068*     (2006.01)
    *A61B 17/29*     (2006.01)
    *A61B 90/00*     (2016.01)
    *A61B 17/064*     (2006.01)

(52) U.S. Cl.
    CPC .............. *A61B 17/8872* (2013.01); *A61B 2017/00367* (2013.01); *A61B 2017/00473* (2013.01); *A61B 2017/0648* (2013.01); *A61B 2017/0649* (2013.01); *A61B 2017/2923* (2013.01); *A61B 2017/2946* (2013.01); *A61B 2090/038* (2016.02)

(58) Field of Classification Search
    CPC .. A61B 2017/00473; A61B 2017/0648; A61B 2017/0649; A61B 2017/2923; A61B 2017/2946
    USPC ........................................................ 227/181.1
    See application file for complete search history.

(56) References Cited

U.S. PATENT DOCUMENTS

| | | | |
|---|---|---|---|
| 4,403,959 A * | 9/1983 | Hatakeyama | A61C 1/18 285/316 |
| 4,577,875 A * | 3/1986 | Miyakawa | B23B 31/06 279/155 |
| 4,730,726 A | 3/1988 | Holzwarth | |
| 4,846,714 A * | 7/1989 | Welsby | H01R 13/62 285/316 |
| 4,884,572 A | 12/1989 | Bays et al. | |
| 5,085,661 A | 2/1992 | Moss | |
| 5,144,942 A | 9/1992 | Decarie et al. | |
| 5,156,267 A | 10/1992 | Yates, Jr. et al. | |
| 5,171,247 A | 12/1992 | Hughett et al. | |
| 5,171,249 A | 12/1992 | Stefanchik et al. | |
| 5,176,306 A | 1/1993 | Heimerl et al. | |
| 5,207,697 A * | 5/1993 | Carusillo | A61B 17/1626 320/115 |
| 5,228,256 A | 7/1993 | Dreveny | |
| 5,236,563 A | 8/1993 | Loh | |
| 5,246,441 A | 9/1993 | Ross | |
| 5,246,450 A | 9/1993 | Thornton et al. | |
| 5,312,023 A | 5/1994 | Green et al. | |
| 5,330,487 A | 7/1994 | Thornton et al. | |
| 5,344,061 A | 9/1994 | Crainich | |
| 5,353,929 A | 10/1994 | Foster | |
| 5,356,064 A * | 10/1994 | Green | A61B 17/0684 227/177.1 |
| 5,381,896 A | 1/1995 | Simons | |
| 5,381,943 A | 1/1995 | Allen et al. | |
| 5,382,254 A | 1/1995 | McGarry et al. | |
| 5,398,861 A | 3/1995 | Green | |
| 5,403,327 A * | 4/1995 | Thornton | A61B 17/1285 227/91 |
| 5,407,070 A | 4/1995 | Bascos et al. | |
| 5,433,721 A | 7/1995 | Hooven et al. | |
| 5,439,468 A | 8/1995 | Schulze et al. | |
| 5,466,243 A | 11/1995 | Schmieding et al. | |
| 5,467,911 A | 11/1995 | Tsuruta et al. | |
| 5,474,566 A | 12/1995 | Alesi et al. | |
| 5,474,567 A | 12/1995 | Stefanchik et al. | |
| 5,478,003 A * | 12/1995 | Green | A61B 17/07207 227/176.1 |
| 5,496,323 A * | 3/1996 | Dye | A61B 17/1659 403/325 |
| 5,505,737 A | 4/1996 | Gosselin et al. | |
| 5,509,695 A * | 4/1996 | Hummel | F16L 37/23 285/23 |
| 5,522,844 A | 6/1996 | Johnson | |
| 5,527,319 A | 6/1996 | Green et al. | |
| 5,553,765 A | 9/1996 | Knodel et al. | |
| 5,562,685 A | 10/1996 | Mollenauer et al. | |
| 5,564,615 A | 10/1996 | Bishop et al. | |
| 5,582,615 A * | 12/1996 | Foshee | A61B 17/2909 606/139 |
| 5,582,616 A | 12/1996 | Bolduc et al. | |
| 5,584,425 A | 12/1996 | Savage et al. | |
| 5,588,581 A | 12/1996 | Conlon et al. | |
| 5,601,571 A | 2/1997 | Moss | |
| 5,601,573 A | 2/1997 | Fogelberg et al. | |
| 5,626,613 A | 5/1997 | Schmieding | |
| 5,628,752 A | 5/1997 | Asnis et al. | |
| 5,649,931 A | 7/1997 | Bryant et al. | |
| 5,662,662 A | 9/1997 | Bishop et al. | |
| 5,681,330 A | 10/1997 | Hughett et al. | |
| 5,683,401 A | 11/1997 | Schmieding et al. | |
| 5,685,474 A | 11/1997 | Seeber | |
| 5,697,935 A | 12/1997 | Moran et al. | |
| 5,709,692 A | 1/1998 | Mollenauer et al. | |
| 5,718,596 A * | 2/1998 | Inaba | H01R 13/6271 439/352 |
| 5,728,116 A | 3/1998 | Rosenman | |
| 5,730,744 A | 3/1998 | Justin et al. | |
| 5,732,806 A | 3/1998 | Foshee et al. | |
| 5,735,854 A | 4/1998 | Caron et al. | |
| 5,741,268 A | 4/1998 | Schutz | |
| 5,762,255 A | 6/1998 | Chrisman et al. | |
| 5,782,844 A | 7/1998 | Yoon et al. | |
| 5,810,882 A | 9/1998 | Bolduc et al. | |
| 5,824,008 A | 10/1998 | Bolduc et al. | |
| 5,830,221 A | 11/1998 | Stein et al. | |
| 5,843,087 A | 12/1998 | Jensen et al. | |
| 5,897,564 A | 4/1999 | Schulze et al. | |
| 5,904,693 A | 5/1999 | Dicesare et al. | |
| 5,910,105 A | 6/1999 | Swain et al. | |
| 5,911,722 A | 6/1999 | Adler et al. | |
| 5,928,241 A * | 7/1999 | Menut | A61B 17/162 279/143 |
| 5,928,244 A | 7/1999 | Tovey et al. | |
| 5,928,252 A | 7/1999 | Steadman et al. | |
| 5,931,844 A | 8/1999 | Thompson et al. | |
| 5,941,439 A | 8/1999 | Kammerer et al. | |
| 5,954,259 A | 9/1999 | Viola et al. | |
| 5,961,524 A | 10/1999 | Crombie | |
| 5,964,772 A | 10/1999 | Bolduc et al. | |
| 5,976,160 A | 11/1999 | Crainich | |
| 5,997,552 A * | 12/1999 | Person | A61B 17/064 606/139 |
| 6,010,513 A | 1/2000 | Tormala et al. | |
| 6,013,991 A | 1/2000 | Philipp | |
| 6,039,753 A | 3/2000 | Meislin | |
| 6,059,598 A * | 5/2000 | Yamashita | H01R 13/6272 403/326 |
| 6,074,395 A | 6/2000 | Trott et al. | |
| 6,099,537 A | 8/2000 | Sugai et al. | |
| 6,109,500 A * | 8/2000 | Alli | A61B 17/07207 227/175.2 |
| 6,126,359 A * | 10/2000 | Dittrich | A61B 17/29 403/325 |
| 6,126,670 A | 10/2000 | Walker et al. | |
| 6,129,392 A * | 10/2000 | Dittrich | A61B 1/00128 285/314 |
| 6,132,435 A | 10/2000 | Young | |
| 6,146,387 A | 11/2000 | Trott et al. | |
| 6,183,479 B1 | 2/2001 | Tormala et al. | |
| 6,228,098 B1 | 5/2001 | Kayan et al. | |
| 6,235,058 B1 | 5/2001 | Huene | |
| 6,241,736 B1 | 6/2001 | Sater et al. | |
| 6,261,302 B1 | 7/2001 | Voegele et al. | |
| 6,296,656 B1 | 10/2001 | Bolduc et al. | |
| 6,325,656 B1 * | 12/2001 | Fukuda | H01R 13/6272 439/358 |
| 6,330,964 B1 | 12/2001 | Kayan et al. | |
| 6,387,113 B1 | 5/2002 | Hawkins et al. | |
| 6,402,757 B1 | 6/2002 | Moore, III et al. | |
| 6,425,900 B1 | 7/2002 | Knodel et al. | |
| 6,439,446 B1 | 8/2002 | Perry et al. | |
| 6,440,136 B1 | 8/2002 | Gambale et al. | |
| 6,450,391 B1 | 9/2002 | Kayan et al. | |
| 6,457,625 B1 | 10/2002 | Tormala et al. | |
| 6,551,333 B2 | 4/2003 | Kuhns et al. | |

(56) References Cited

U.S. PATENT DOCUMENTS

| | | | |
|---|---|---|---|
| 6,562,051 B1 | 5/2003 | Bolduc et al. | |
| 6,572,626 B1 | 6/2003 | Knodel et al. | |
| 6,589,249 B2 | 7/2003 | Sater et al. | |
| 6,592,593 B1 | 7/2003 | Parodi et al. | |
| 6,626,916 B1 | 9/2003 | Yeung et al. | |
| 6,632,228 B2 | 10/2003 | Fortier et al. | |
| 6,652,538 B2 | 11/2003 | Kayan et al. | |
| 6,663,656 B2 | 12/2003 | Schmieding et al. | |
| 6,666,854 B1 | 12/2003 | Lange | |
| 6,695,867 B2 | 2/2004 | Ginn et al. | |
| 6,706,056 B2 * | 3/2004 | Bacher | A61B 17/29 606/208 |
| 6,733,506 B1 | 5/2004 | McDevitt et al. | |
| 6,743,240 B2 | 6/2004 | Smith et al. | |
| 6,749,621 B2 | 6/2004 | Pantages et al. | |
| 6,755,836 B1 | 6/2004 | Lewis | |
| 6,773,438 B1 | 8/2004 | Knodel et al. | |
| 6,800,081 B2 | 10/2004 | Parodi | |
| 6,824,548 B2 | 11/2004 | Smith et al. | |
| 6,837,893 B2 | 1/2005 | Miller | |
| 6,840,943 B2 | 1/2005 | Kennefick et al. | |
| 6,843,794 B2 | 1/2005 | Sixto, Jr. et al. | |
| 6,869,435 B2 | 3/2005 | Blake, III | |
| 6,884,248 B2 | 4/2005 | Bolduc et al. | |
| 6,887,244 B1 | 5/2005 | Walker et al. | |
| 6,893,446 B2 | 5/2005 | Sater et al. | |
| 6,905,057 B2 | 6/2005 | Swayze et al. | |
| 6,929,661 B2 | 8/2005 | Bolduc et al. | |
| 6,942,674 B2 | 9/2005 | Belef et al. | |
| 6,945,979 B2 | 9/2005 | Kortenbach et al. | |
| 6,953,139 B2 * | 10/2005 | Milliman | A61B 17/07207 227/175.1 |
| 6,960,217 B2 | 11/2005 | Bolduc | |
| 6,966,919 B2 | 11/2005 | Sixto, Jr. et al. | |
| 6,984,143 B2 * | 1/2006 | Roese | H01R 13/6273 439/352 |
| 6,988,650 B2 | 1/2006 | Schwemberger et al. | |
| 7,000,819 B2 | 2/2006 | Swayze et al. | |
| 7,128,253 B2 * | 10/2006 | Mastri | A61B 17/0684 227/176.1 |
| 7,128,754 B2 | 10/2006 | Bolduc | |
| 7,159,750 B2 * | 1/2007 | Racenet | A61B 17/07207 227/180.1 |
| 7,204,847 B1 | 4/2007 | Gambale | |
| 7,229,306 B2 * | 6/2007 | Mase | H01R 13/6272 439/354 |
| 7,252,530 B2 * | 8/2007 | Shamoto | H01R 13/641 439/352 |
| 7,261,716 B2 | 8/2007 | Strobel et al. | |
| 7,296,804 B2 * | 11/2007 | Lechot | A61B 17/1666 279/140 |
| 7,491,232 B2 | 2/2009 | Bolduc et al. | |
| 7,614,904 B2 * | 11/2009 | Hiramatsu | H01R 13/641 439/352 |
| 7,670,362 B2 | 3/2010 | Zergiebel | |
| 7,758,612 B2 | 7/2010 | Shipp | |
| 7,766,929 B2 * | 8/2010 | Masuda | A61B 17/320092 604/22 |
| 7,810,817 B1 * | 10/2010 | Gao | B23B 31/1071 279/75 |
| 7,862,573 B2 | 1/2011 | Darois et al. | |
| 7,867,252 B2 | 1/2011 | Criscuolo et al. | |
| 7,931,660 B2 | 4/2011 | Aranyi et al. | |
| 8,002,811 B2 | 8/2011 | Corradi et al. | |
| 8,034,076 B2 | 10/2011 | Criscuolo et al. | |
| 8,075,570 B2 | 12/2011 | Bolduc et al. | |
| 8,087,142 B2 | 1/2012 | Levin et al. | |
| 8,114,099 B2 | 2/2012 | Shipp | |
| 8,114,101 B2 | 2/2012 | Criscuolo et al. | |
| 8,216,272 B2 | 7/2012 | Shipp | |
| 8,231,639 B2 | 7/2012 | Bolduc et al. | |
| 8,282,670 B2 | 10/2012 | Shipp | |
| 8,292,933 B2 | 10/2012 | Zergiebel | |
| 8,323,314 B2 | 12/2012 | Blier | |
| 8,328,823 B2 | 12/2012 | Aranyi et al. | |
| 8,343,176 B2 | 1/2013 | Criscuolo et al. | |
| 8,343,184 B2 | 1/2013 | Blier | |
| 8,382,778 B2 | 2/2013 | Criscuolo et al. | |
| 8,414,627 B2 | 4/2013 | Corradi et al. | |
| 8,465,520 B2 | 6/2013 | Blier | |
| 8,469,423 B1 * | 6/2013 | Crowley, Jr. | B25G 1/04 294/174 |
| 8,474,679 B2 | 7/2013 | Felix | |
| 8,579,919 B2 | 11/2013 | Bolduc et al. | |
| 8,579,920 B2 | 11/2013 | Nering et al. | |
| 8,597,311 B2 | 12/2013 | Criscuolo et al. | |
| 8,728,120 B2 | 5/2014 | Blier | |
| 8,777,969 B2 | 7/2014 | Kayan | |
| 8,821,522 B2 | 9/2014 | Criscuolo et al. | |
| 8,821,557 B2 | 9/2014 | Corradi et al. | |
| 8,844,942 B1 * | 9/2014 | Landowski | B25G 3/12 279/22 |
| 8,852,215 B2 | 10/2014 | Criscuolo et al. | |
| 8,968,311 B2 | 3/2015 | Allen, IV et al. | |
| 9,186,138 B2 | 11/2015 | Corradi et al. | |
| 9,259,221 B2 | 2/2016 | Zergiebel | |
| 9,265,516 B2 * | 2/2016 | Casey | A61B 17/32 |
| 9,655,621 B2 | 5/2017 | Abuzaina et al. | |
| 9,662,106 B2 | 5/2017 | Corradi et al. | |
| 9,668,730 B2 * | 6/2017 | Sniffin | A61B 17/068 |
| 9,705,253 B2 * | 7/2017 | Horiuchi | H01R 13/641 |
| 9,783,329 B2 * | 10/2017 | Sniffin | B65B 5/10 |
| 9,801,633 B2 | 10/2017 | Sholev et al. | |
| 9,867,620 B2 * | 1/2018 | Fischvogt | A61B 17/12013 |
| 9,877,763 B2 * | 1/2018 | Barth | A61B 17/8866 |
| 9,987,010 B2 | 6/2018 | Zergiebel | |
| 10,070,860 B2 | 9/2018 | Zergiebel | |
| 2002/0058958 A1 * | 5/2002 | Walen | A61B 17/1615 606/170 |
| 2002/0095177 A1 * | 7/2002 | Kupferschmid | A61B 17/29 606/205 |
| 2003/0009441 A1 | 1/2003 | Holsten et al. | |
| 2003/0060841 A1 | 3/2003 | Del Rio et al. | |
| 2003/0114839 A1 | 6/2003 | Looper et al. | |
| 2004/0092937 A1 | 5/2004 | Criscuolo et al. | |
| 2004/0111089 A1 | 6/2004 | Stevens et al. | |
| 2004/0127916 A1 | 7/2004 | Bolduc et al. | |
| 2004/0181222 A1 | 9/2004 | Culbert et al. | |
| 2004/0243139 A1 | 12/2004 | Lewis et al. | |
| 2006/0041268 A1 | 2/2006 | Shores et al. | |
| 2006/0053974 A1 * | 3/2006 | Blust | A61B 17/162 81/3.07 |
| 2006/0100629 A1 | 5/2006 | Lee | |
| 2006/0129152 A1 | 6/2006 | Shipp | |
| 2006/0129154 A1 | 6/2006 | Shipp | |
| 2006/0259070 A1 * | 11/2006 | Livneh | A61B 17/1608 606/205 |
| 2007/0031184 A1 * | 2/2007 | Baxstrom | F16B 7/042 403/109.3 |
| 2007/0038220 A1 | 2/2007 | Shipp | |
| 2007/0162030 A1 | 7/2007 | Aranyi et al. | |
| 2008/0086154 A1 | 4/2008 | Taylor et al. | |
| 2008/0097523 A1 | 4/2008 | Bolduc et al. | |
| 2008/0147113 A1 | 6/2008 | Nobis et al. | |
| 2008/0188868 A1 | 8/2008 | Weitzner et al. | |
| 2008/0243106 A1 | 10/2008 | Coe et al. | |
| 2008/0243133 A1 * | 10/2008 | Heinz | A61B 17/7082 606/104 |
| 2008/0281336 A1 * | 11/2008 | Zergiebel | A61B 17/068 606/142 |
| 2008/0312687 A1 | 12/2008 | Blier | |
| 2009/0118776 A1 | 5/2009 | Kelsch et al. | |
| 2009/0149054 A1 * | 6/2009 | Zheng | H01R 13/6272 439/357 |
| 2009/0188965 A1 | 7/2009 | Levin et al. | |
| 2010/0030262 A1 | 2/2010 | McLean et al. | |
| 2010/0237133 A1 * | 9/2010 | Shah | A61B 17/07207 227/181.1 |
| 2010/0270354 A1 | 10/2010 | Rimer et al. | |
| 2010/0292710 A1 | 11/2010 | Daniel et al. | |
| 2010/0292713 A1 | 11/2010 | Cohn et al. | |
| 2010/0292715 A1 | 11/2010 | Nering et al. | |

(56) References Cited

U.S. PATENT DOCUMENTS

| | | |
|---|---|---|
| 2011/0022065 A1 | 1/2011 | Shipp |
| 2011/0060349 A1 | 3/2011 | Cheng et al. |
| 2011/0071578 A1 | 3/2011 | Colesanti et al. |
| 2011/0079627 A1 | 4/2011 | Cardinale et al. |
| 2011/0087240 A1 | 4/2011 | Shipp |
| 2011/0098688 A1* | 4/2011 | Gigon .................. A61B 17/162 606/1 |
| 2011/0108605 A1* | 5/2011 | Sapienza .......... A61B 17/07207 227/180.1 |
| 2011/0204120 A1 | 8/2011 | Crainich |
| 2011/0295282 A1 | 12/2011 | Glick et al. |
| 2012/0059397 A1 | 3/2012 | Criscuolo et al. |
| 2012/0076577 A1* | 3/2012 | Yanagihara ........ A61B 1/00087 403/375 |
| 2012/0109157 A1 | 5/2012 | Criscuolo et al. |
| 2012/0116388 A1* | 5/2012 | Houser ............ A61B 17/00234 606/41 |
| 2013/0018392 A1 | 1/2013 | Zergiebel |
| 2013/0110088 A1 | 5/2013 | Wenchell |
| 2013/0131700 A1 | 5/2013 | Criscuolo et al. |
| 2013/0197591 A1 | 8/2013 | Corradi et al. |
| 2014/0114329 A1 | 4/2014 | Zergiebel |
| 2014/0121684 A1 | 5/2014 | Criscuolo et al. |
| 2014/0276949 A1* | 9/2014 | Staunton .......... A61B 17/32002 606/130 |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0012014 A1* | 1/2015 | Williams ......... A61B 17/07207 606/143 |
| 2015/0018847 A1 | 1/2015 | Criscuolo et al. |
| 2015/0032130 A1 | 1/2015 | Russo |
| 2015/0053740 A1 | 2/2015 | Shelton, IV |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |
| 2015/0150558 A1 | 6/2015 | Zergiebel |
| 2015/0201949 A1* | 7/2015 | Barth .................... A61B 17/162 606/80 |
| 2015/0238241 A1* | 8/2015 | Barth .................... A61B 17/162 606/86 R |
| 2015/0238242 A1* | 8/2015 | Barth .................... A61B 17/162 606/86 R |
| 2015/0297199 A1* | 10/2015 | Nicholas ................ A61B 17/00 606/1 |
| 2015/0327859 A1 | 11/2015 | Bolduc |
| 2016/0007991 A1 | 1/2016 | Bolduc |
| 2016/0007996 A1 | 1/2016 | Bolduc |
| 2016/0066971 A1 | 3/2016 | Corradi et al. |
| 2016/0074034 A1 | 3/2016 | Shipp |
| 2016/0106463 A1* | 4/2016 | Egle ...................... F16B 7/20 606/119 |
| 2017/0042657 A1 | 2/2017 | Criscuolo et al. |
| 2017/0128068 A1 | 5/2017 | Zhang et al. |
| 2017/0151048 A1 | 6/2017 | Russo |
| 2017/0231631 A1 | 8/2017 | Abuzaina et al. |
| 2017/0265859 A1* | 9/2017 | Sniffin ................. A61B 17/068 |
| 2018/0042591 A1 | 2/2018 | Russo et al. |
| 2018/0116670 A1 | 5/2018 | Fischvogt et al. |
| 2018/0146972 A1* | 5/2018 | Merza .................. A61B 17/32 |

FOREIGN PATENT DOCUMENTS

| | | |
|---|---|---|
| CN | 101106945 A | 1/2008 |
| CN | 203379164 U | 1/2014 |
| DE | 10300787 A1 | 9/2004 |
| DE | 10 2010 015009 A1 | 10/2011 |
| EP | 0374088 A1 | 6/1990 |
| EP | 0834280 A1 | 4/1998 |
| EP | 1273272 A2 | 1/2003 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| EP | 2853202 A2 | 4/2015 |
| JP | 09149906 | 6/1997 |
| JP | 2006525061 A | 11/2006 |
| WO | 00/16701 A1 | 3/2000 |
| WO | 2002/034140 A2 | 5/2002 |
| WO | 2003/034925 A2 | 5/2003 |
| WO | 2003/103507 A2 | 12/2003 |
| WO | 2004/112841 A2 | 12/2004 |
| WO | 2005004727 A1 | 1/2005 |
| WO | 2009/039506 A1 | 3/2009 |
| WO | 2012/064692 A2 | 5/2012 |
| WO | 2013/046115 A1 | 4/2013 |

OTHER PUBLICATIONS

European Office Action corresponding to counterpart Int'l Appln. No. EP 14 19 7885.8 dated Feb. 7, 2017.
Chinese First Office Action corresponding to counterpart Int'l Appln. No. CN 201410090675 dated Feb. 28, 2017.
Extended European Search Report corresponding to counterpart Int'l Appln. No. EP 16 19 8333.3 dated Mar. 15, 2017.
European Office Action corresponding to counterpart Int'l Appln. No. EP 14 15 1663.3 dated May 10, 2017.
Extended European Search Report corresponding to counterpart Int'l Appln. No. EP 17 15 7259.7 dated May 10, 2017.
Chinese First Office Action corresponding to counterpart Int'l Appln. No. CN 2014103559671 dated Jun. 13, 2017.
Australian Examination Report No. 1 corresponding to counterpart Int'l Appln. No. AU 2014200071 dated Jun. 20, 2017.
Australian Examination Report No. 1 corresponding to counterpart Int'l Appln. No. AU 2014201338 dated Jul. 10, 2017.
Extended European Search Report corresponding to counterpart application EP 10 01 2659.8, completed Dec. 21, 2010 and dated Jan. 3, 2011; 3 pages.
Extended European Search Report corresponding to counterpart application EP 10 01 2646.5, completed Feb. 11, 2011 and dated Feb. 22, 2011; 10 pages.
Extended European Search Report corresponding to counterpart application EP 11 25 0549.0, completed Sep. 9, 2013 and dated Sep. 17, 2013; 9 pages.
Extended European Search Report corresponding to counterpart application EP 14 15 9394.7, completed Apr. 16, 2014 and dated Apr. 29, 2014; 8 pages.
Extended European Search Report corresponding to counterpart application EP 14 15 8946.5, completed Jun. 20, 2014 and dated Jul. 8, 2014; (9 pp).
Extended European Search Report corresponding to counterpart application EP 14 17 8107.0, completed Nov. 24, 2014 and dated Dec. 3, 2014; (5 pp).
Extended European Search Report corresponding to counterpart application EP 14 17 4656.0, completed Jan. 16, 2015 and dated Jan. 26, 2015; (7 pp).
Extended European Search Report corresponding to counterpart application EP 14 18 4907.5, completed Jan. 12, 2015 and dated Jan. 27, 2015; (9 pp).
Extended European Search Report corresponding to counterpart Int'l Application No. EP 14 18 1900.3 dated Apr. 9, 2015.
Extended European Search Report corresponding to counterpart Int'l Application No. EP 14 19 7885.8 dated Mar. 30, 2015.
Chinese First Office Action corresponding to Chinese Patent Appln. No. 201480037169.2 dated Jun. 29, 2017.
Chinese First Office Action corresponding to Chinese Patent Appln. No. 201410418879.1 dated Jun. 29, 2017.
European Office Action corresponding to European Patent Appln. No. 14 17 8107.0 dated Oct. 12, 2017.

(56) References Cited

OTHER PUBLICATIONS

Australian Examination Report No. 1 corresponding to Australian Patent Appln. No. 2014200870 dated Oct. 26, 2017.
Chinese Second Office Action corresponding to Chinese Patent Appln. No. 201410090675 dated Nov. 6, 2017.
Japanese Office Action corresponding to Japanese Patent Appln. No. 2014-048652 dated Nov. 14, 2017.
Japanese Office Action corresponding to Japanese Patent Appln. No. 2014-047708 dated Nov. 14, 2017.
Chinese Second Office Action corresponding to Chinese Patent Appln. No. 2014103063407 dated Feb. 1, 2018.
Australian Examination Report No. 1 corresponding to Australian Patent Appln. No. 2014202970 dated Mar. 9, 2018.
Japanese Office Action corresponding to Japanese Patent Appln. No. 2014-048652 dated Mar. 15, 2018.
Chinese Second Office Action corresponding to Chinese Patent Appln. No. 201480077682.4 dated Mar. 21, 2018.
Australian Examination Report No. 1 corresponding to Australian Patent Appln. No. 2014202972 dated Mar. 27, 2018.
European Office Action corresponding to Patent Application EP 14 15 8946.5 dated Apr. 26, 2018.
Japanese Office Action corresponding to Patent Application JP 2014-132105 dated May 1, 2018.
Japanese Office Action corresponding to Patent Application JP 2014-047708 dated May 14, 2018.
Chinese Second Office Action corresponding to Patent Application CN 2014103559671 dated May 25, 2018.
Australian Examination Report No. 1 corresponding to Patent Application AU 2014302551 dated Jul. 16, 2018.
Japanese Office Action corresponding to Patent Application JP 2014-047708 dated Aug. 15, 2018.
Japanese Office Action issued in corresponding Japanese Application No. 2016-046868 dated Jan. 17, 2020, 10 pages.
Australian Examination Report issued in corresponding Australian Application No. 2016201340 dated Aug. 29, 2019, 4 pages.
Chinese Office Action issued in Chinese Application No. 2016101539047 dated Aug. 29, 2019, 12 pages.

* cited by examiner

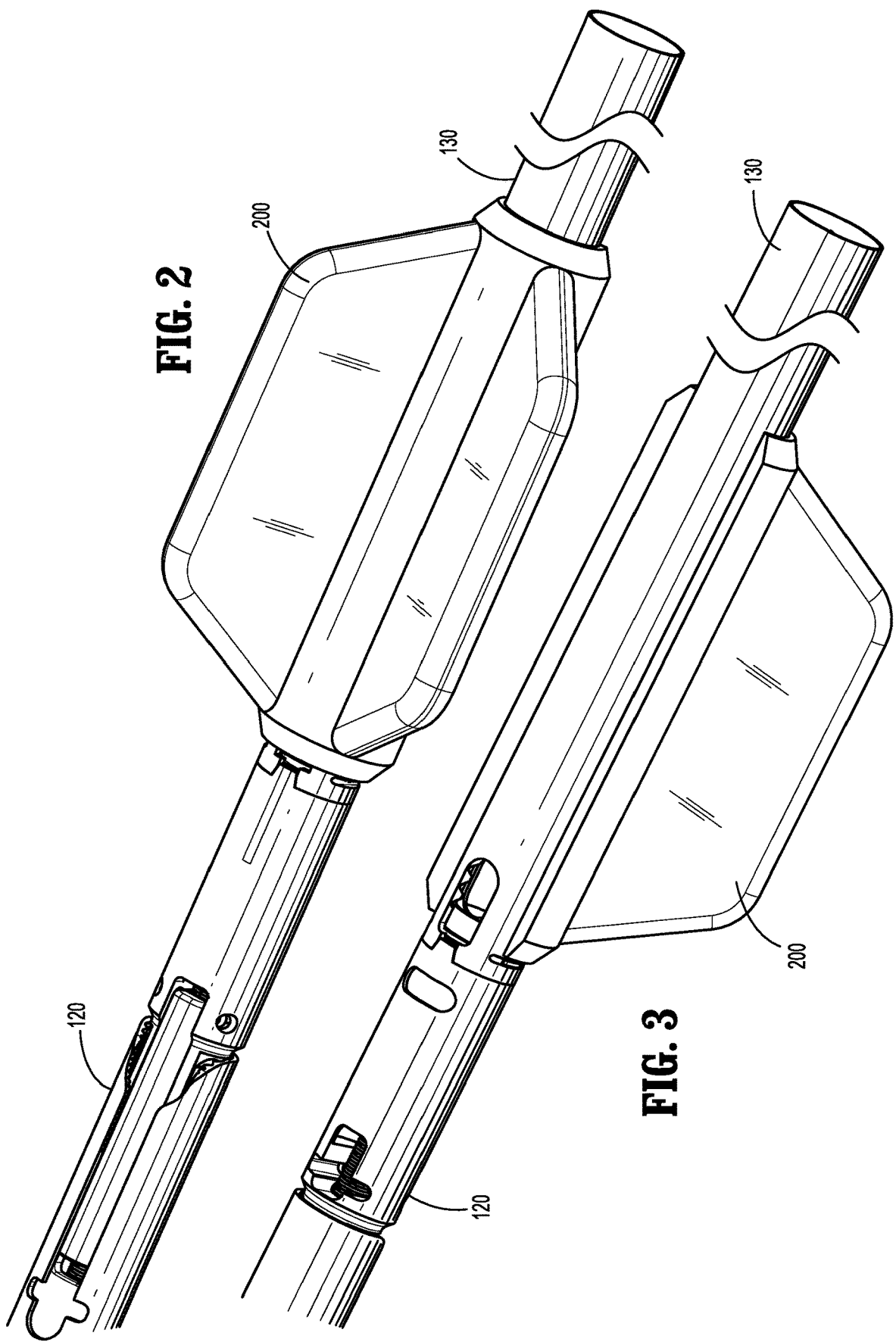

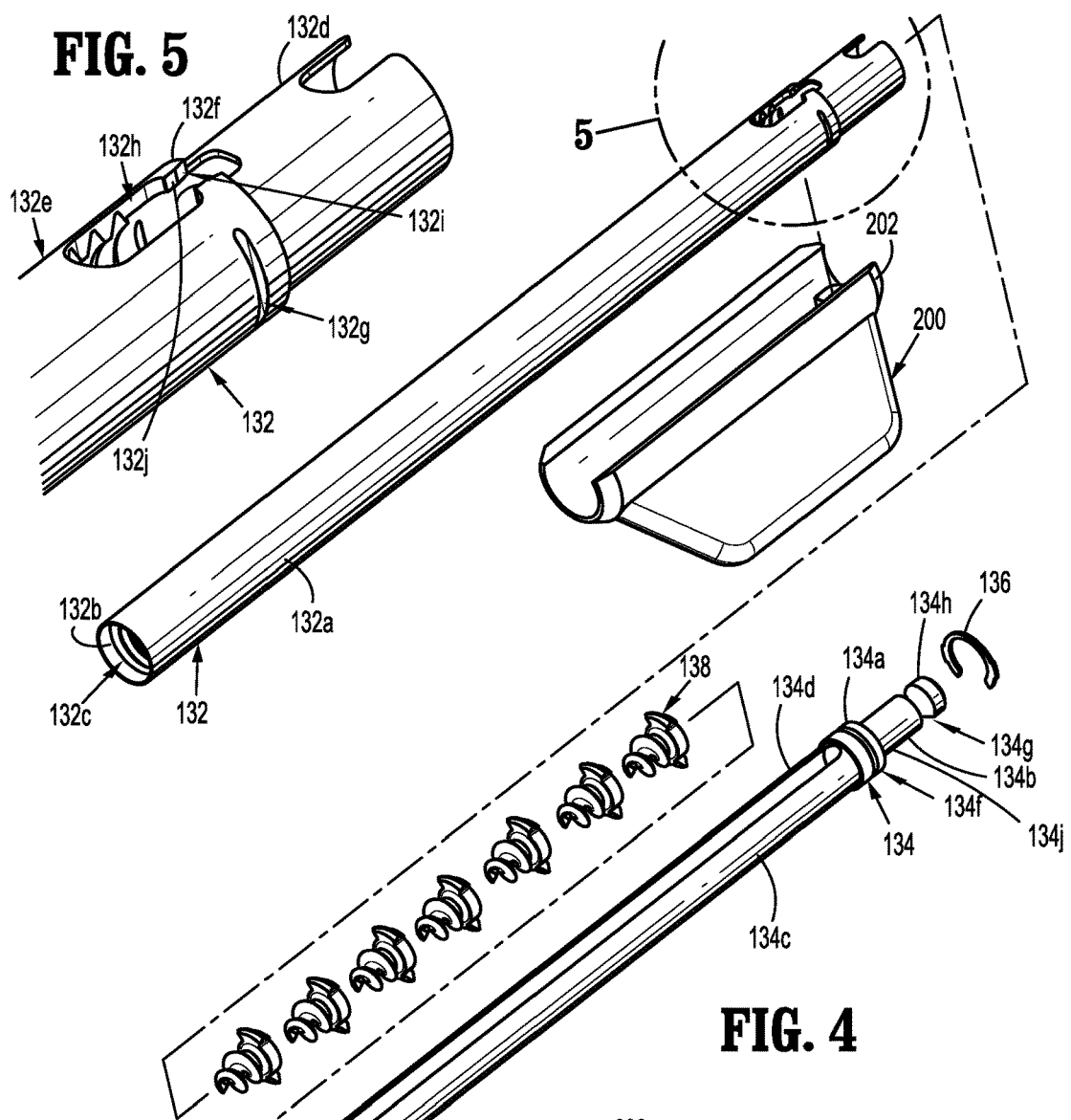
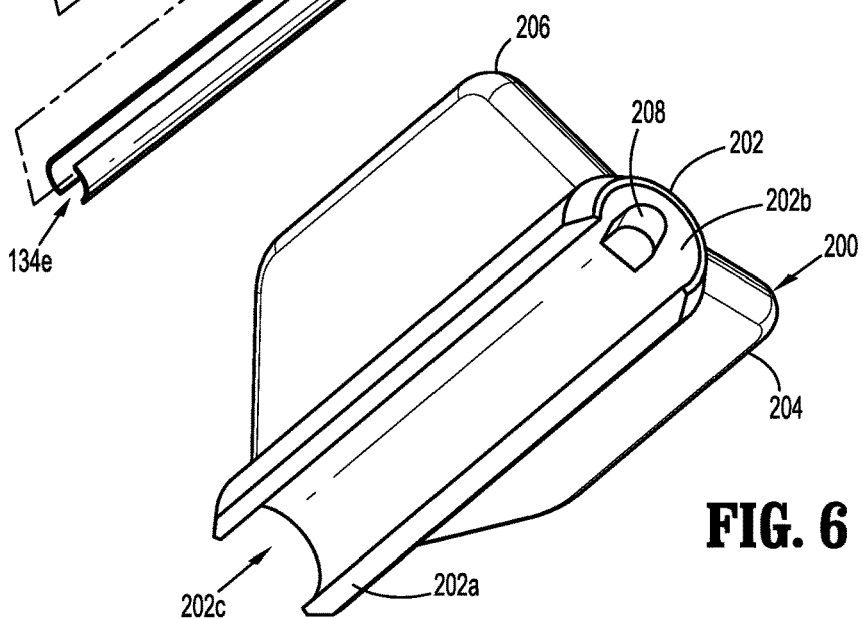

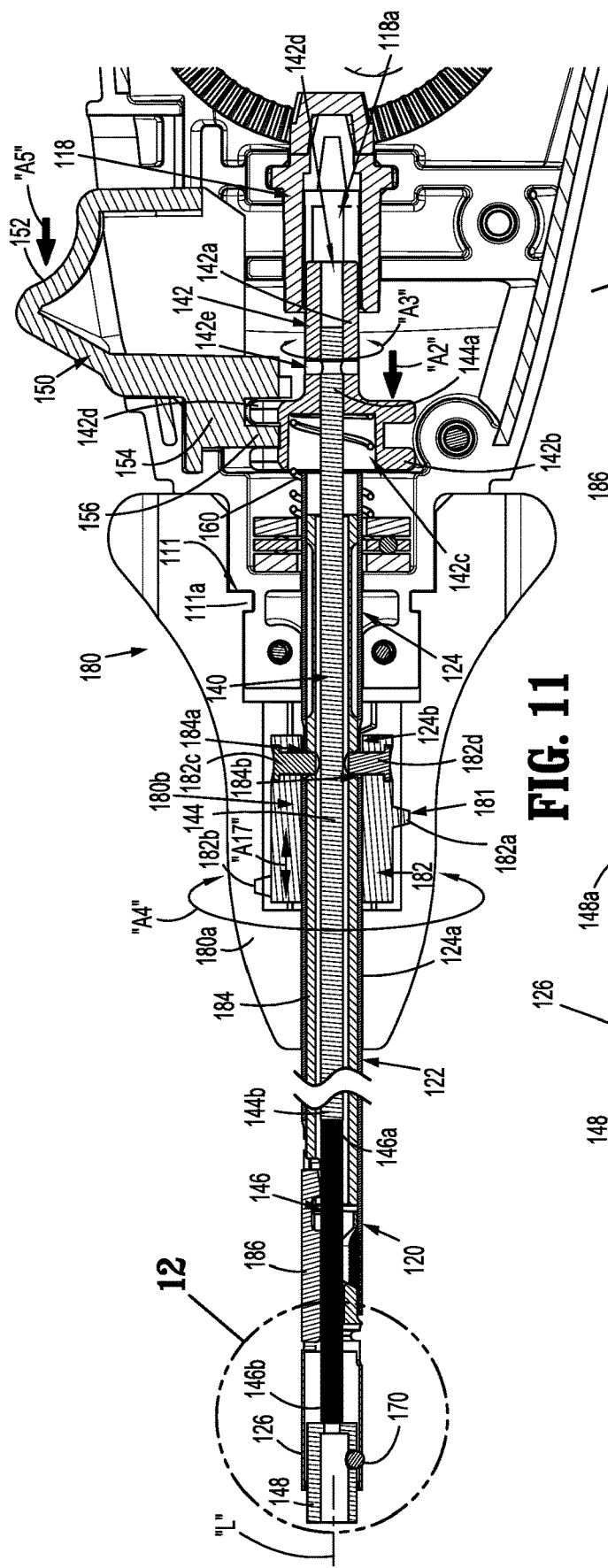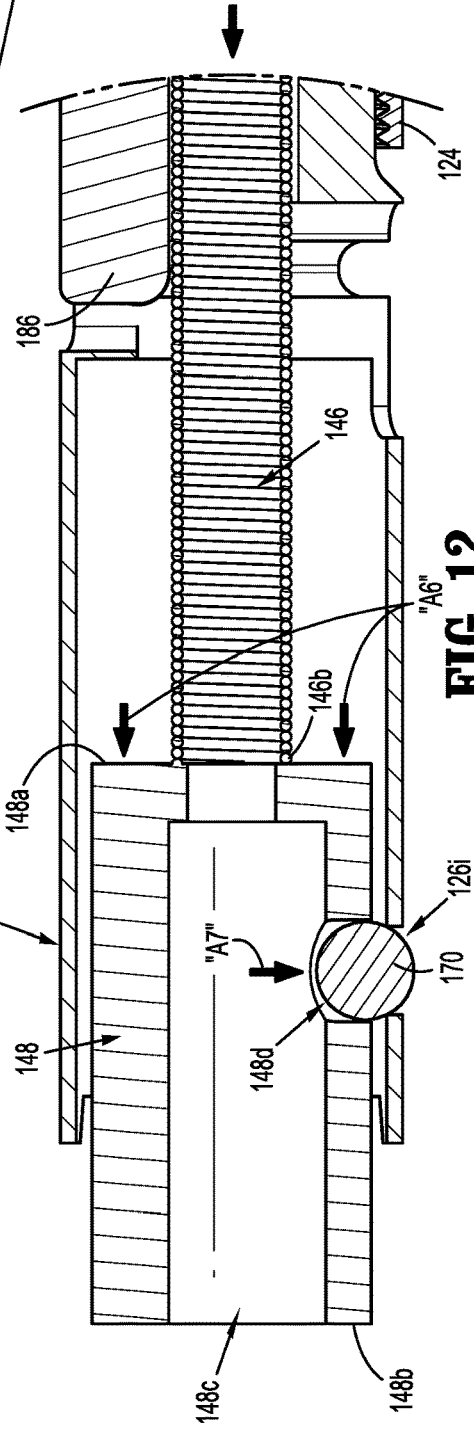
FIG. 11
FIG. 12

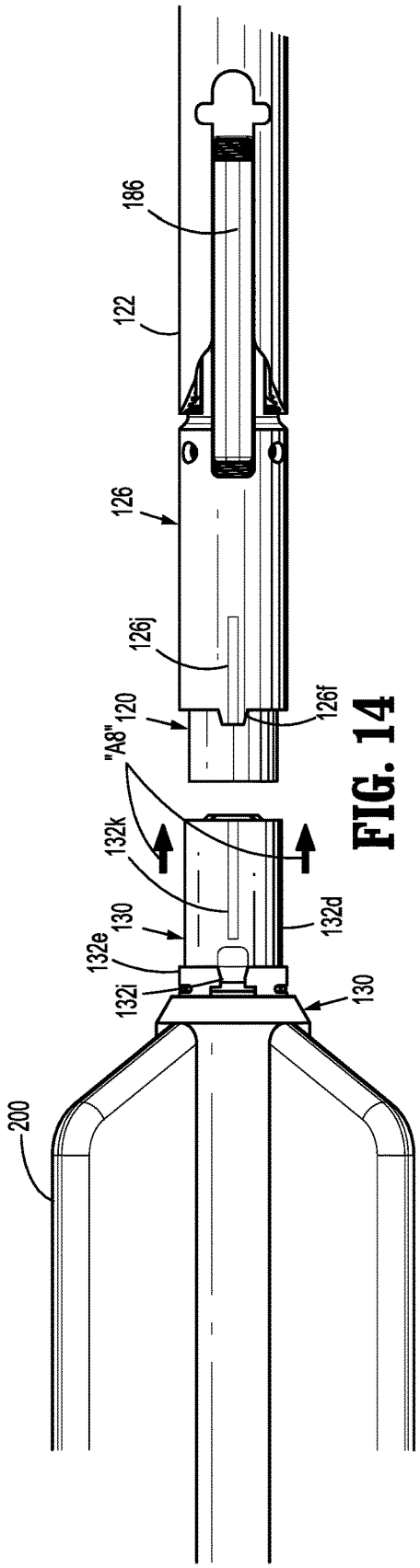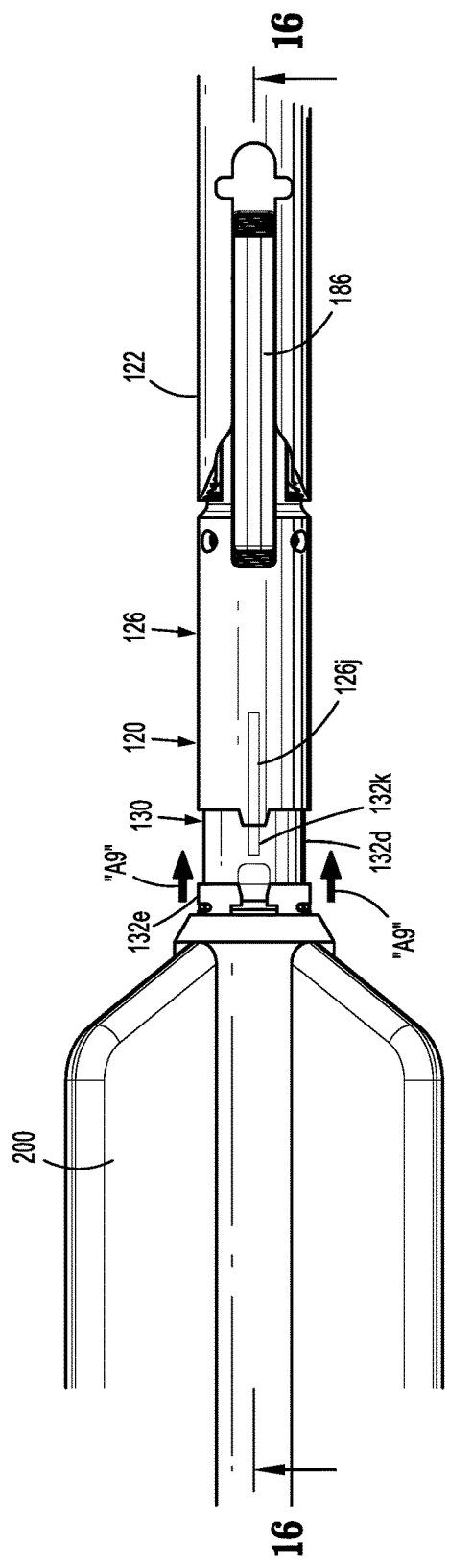

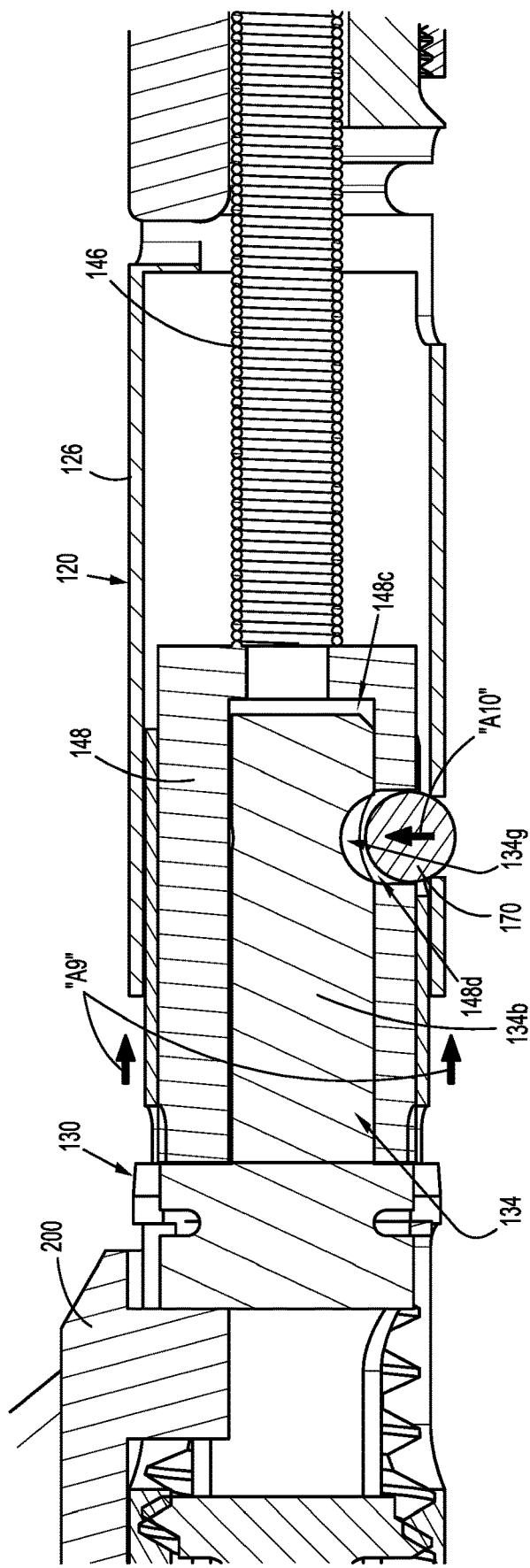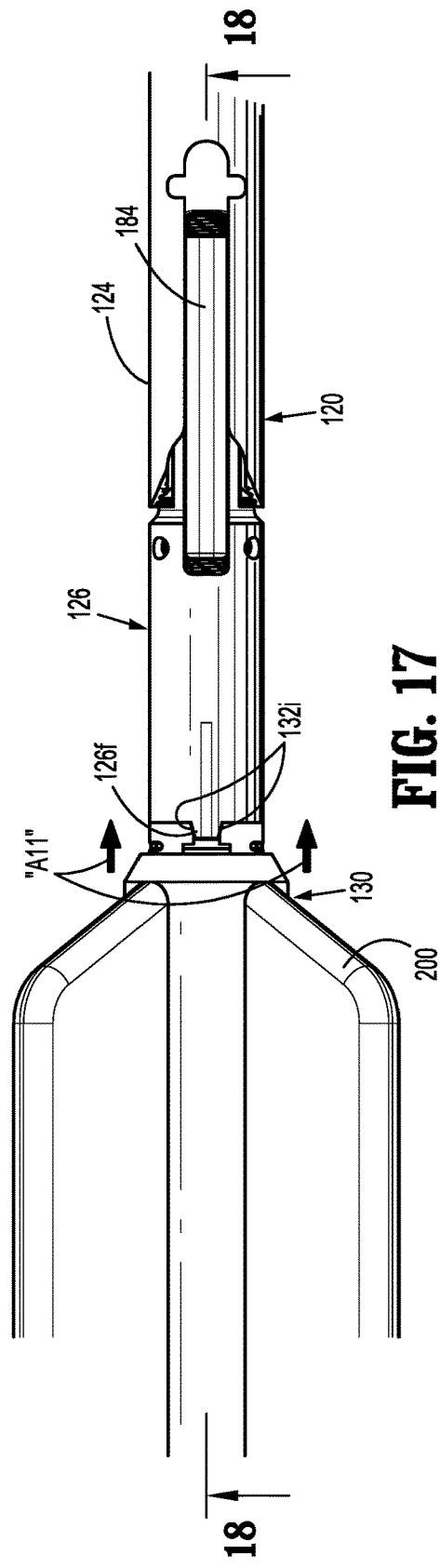

CONNECTING END EFFECTORS TO SURGICAL DEVICES

CROSS-REFERENCE TO RELATED APPLICATIONS

This application claims the benefit of and priority to U.S. Provisional Patent Application Ser. No. 62/134,107 filed Mar. 17, 2015, the entire disclosure of which is incorporated by reference herein.

TECHNICAL FIELD

The present disclosure relates to surgical devices, systems, and/or methods for performing surgical procedures. More specifically, the present disclosure relates to surgical fastener applying devices and/or systems that are loadable with end effectors containing absorbable or permanent surgical fasteners for performing minimally invasive surgical procedures, and methods of use thereof.

BACKGROUND

Various surgical procedures require devices capable of applying fasteners to tissue to form tissue connections or to secure objects to tissue. For example, during hernia repair it is often desirable to fasten a mesh to body tissue. In certain hernias, such as direct or indirect inguinal hernias, a part of the intestine protrudes through a defect in the abdominal wall to form a hernial sac. The defect may be repaired using an open surgery procedure in which a relatively large incision is made and the hernia is closed outside the abdominal wall by suturing. The mesh is attached with sutures over the opening in the abdominal wall to provide reinforcement.

Minimally invasive, e.g., endoscopic or laparoscopic, surgical procedures are currently available to repair a hernia. In laparoscopic procedures, surgery is performed in the abdomen through a small incision while in endoscopic procedures, surgery is performed through narrow endoscopic tubes or cannulas inserted through small incisions in the body. Laparoscopic and endoscopic procedures generally utilize long and narrow devices capable of reaching remote regions within the body and are configured to form a seal with the incision or tube they are inserted through. Additionally, the devices are typically capable of being actuated remotely, that is, from outside the body.

Currently, minimally invasive surgical techniques for hernia repair utilize surgical fasteners, e.g., surgical tacks, staples, and clips, to secure the mesh to the tissue to provide reinforcement and structure for encouraging tissue ingrowth. Surgical fasteners are often applied through an elongated device for delivery to the mesh, and are manipulated from outside a body cavity.

In some procedures permanent fasteners may be required, while in other procedures bioabsorbable fasteners may be required, or both. The minimally invasive devices include end effectors that are typically loaded with either permanent fasteners or bioabsorbable fasteners. Additionally, following a surgical procedure, these devices are either re-sterilized for re-use or are disposed.

SUMMARY

Accordingly, new devices and/or systems that are reliable, precise, and that enable easy and efficient attachment and removal of end effectors thereto, as well as methods of use thereof, would be desirable.

The present disclosure is directed to new devices, systems, and/or methods for enabling attachment and/or detachment of end effectors to surgical devices and/or systems within small work spaces (e.g., 0.218 inch work envelope or the like). The new devices, systems, and/or methods advantageously enable a user to effectuate such attachment and/or detachment remotely from handles thereof by virtue a selectively movable and/or floating detent that couples a proximally extending drive shaft of the end effector to an inner shaft assembly of an elongated body portion of the presently disclosed devices and/or systems. With the presently disclosed end effectors attached to the presently disclosed devices and/or systems, a user can articulate the end effectors relative to the presently disclosed devices and/or systems and/or fire anchors from these end effectors, for example, to secure a mesh to body tissue.

In one aspect of the present disclosure, a surgical device is provided. The surgical device includes an elongated body portion, an end effector, and a detent.

The elongated body portion includes an outer tube and an inner shaft assembly. The outer tube includes a proximal portion and a distal portion. The inner shaft assembly is longitudinally and/or rotationally movable through the outer tube. The inner shaft assembly includes a distal tube defining a non-circular bore in a distal end thereof. The bore may have a D-shaped cross-sectional profile. The outer tube and the distal tube define corresponding openings extending transversely therethrough. The inner shaft assembly includes a proximal rigid portion connected to a distal flexible portion. The distal flexible portion extends distally to the distal tube.

The end effector is selectively connectable to the elongated body portion. The end effector includes a drive shaft that extends proximally therefrom and that defines an annular recess in an outer surface thereof. The annular recess of the drive shaft may have an arcuate cross-sectional profile. The annular recess of the drive shaft may partially circumscribe the drive shaft. The drive shaft has a non-circular transverse cross-sectional profile that is complimentary in shape to the non-circular bore of the inner shaft assembly of the elongated body portion. The non-circular transverse cross-sectional profile of the drive shaft may be D-shaped and may be complementary to D-shaped cross-sectional profile of the bore. The drive shaft rotates in response to rotation of the inner shaft assembly.

The end effector includes an outer housing positioned about the drive shaft. The outer housing of the end effector and the outer tube of the elongated body portion include corresponding mating structures configured and dimensioned for engagement to rotationally align and lock together the elongated body portion and the end effector.

The detent is movable within the openings of the elongated body portion. The detent is positionable between the annular recess of the drive shaft and the outer tube of the elongated body portion to connect the end effector to the elongated body portion in response to insertion of the drive shaft into the non-circular bore of the inner shaft assembly. The detent is configured and dimensioned to float between the end effector and the elongated body portion to enable to selective connection between the end effector and the elongated body portion. In certain embodiments, the detent has a spherical shape.

In some embodiments, the surgical device includes an articulation assembly having an articulation actuator supported at a proximal end of the elongated body portion. A drive assembly is operatively coupled between the articulation actuator and the distal portion of the outer tube. The articulation actuator is actuatable to articulate the distal portion of the outer tube relative to the proximal portion of the outer tube for articulating the end effector relative to a longitudinal axis defined through the elongated body portion.

The drive assembly may include a slidable tube and an articulation arm. The articulation arm is pivotally coupled to the slidable tube and the distal portion of the outer tube. The articulation actuator is coupled to the slidable tube so that rotation of the articulation actuator longitudinal translates the slidable tube through the elongated body portion. Longitudinal translation of the slidable tube longitudinally translates the articulation arm to enable the end effector to articulate relative to the longitudinal axis.

According to yet another aspect, an end effector is configured and dimensioned for releasable connection to an elongated body portion of a surgical fastener applying device. The elongated body portion includes a detent. The end effector includes a proximally extending drive shaft configured and dimensioned for insertion into the elongated body portion of the surgical fastener applying device. The drive shaft defines an annular recess configured and dimensioned to receive the detent such that the detent is positionable between the annular recess and the elongated body portion of the surgical fastener applying device to connect the end effector to the surgical fastener applying device.

The end effector may include an outer tube supporting the proximally extending drive shaft. In some embodiments, the drive shaft is rotatable to fire a plurality of fasteners supported within the outer tube from the outer tube.

According to still another aspect, a surgical fastener applying device configured and dimensioned for releasable connection to an end effector is provided.

The surgical fastener applying device includes an elongated body portion and a detent. The elongated body portion includes an outer tube and an inner shaft assembly. The inner shaft assembly includes a distal tube that defines a non-circular bore in a distal end thereof. The inner shaft assembly is longitudinally movable through the outer tube. The outer tube and the distal tube define corresponding openings extending transversely therethrough. The detent is movable within the openings of the elongated body portion. The detent is configured and dimensioned to float between the end effector and the elongated body portion to enable selective connection between the end effector and the elongated body portion.

Other aspects, features, and advantages will be apparent from the description, the drawings, and the claims that follow.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description given below, serve to explain the principles of the disclosure, wherein:

FIG. 2 is an enlarged, top perspective view of a distal portion of the endoscopic surgical system of FIG. 1;

FIG. 3 is a bottom perspective view of the distal portion of the endoscopic surgical system shown in FIG. 2;

FIG. 4 is a perspective view, with parts separated, of an end effector of the endoscopic surgical system of FIG. 1;

FIG. 5 is an enlarged perspective view of the indicated area of detail shown in FIG. 4.

FIG. 6 is a perspective view of a shipping wedge of the endoscopic surgical system of FIG. 1;

FIG. 11 is a cross-sectional view of a portion of the endoscopic surgical system of FIG. 1 in a second state;

FIG. 12 is an enlarged view of the indicated area of detail shown in FIG. 11;

FIGS. 13-18 are progressive views illustrating an assembly of the endoscopic surgical system of FIG. 1.

DETAILED DESCRIPTION

Figure 1:
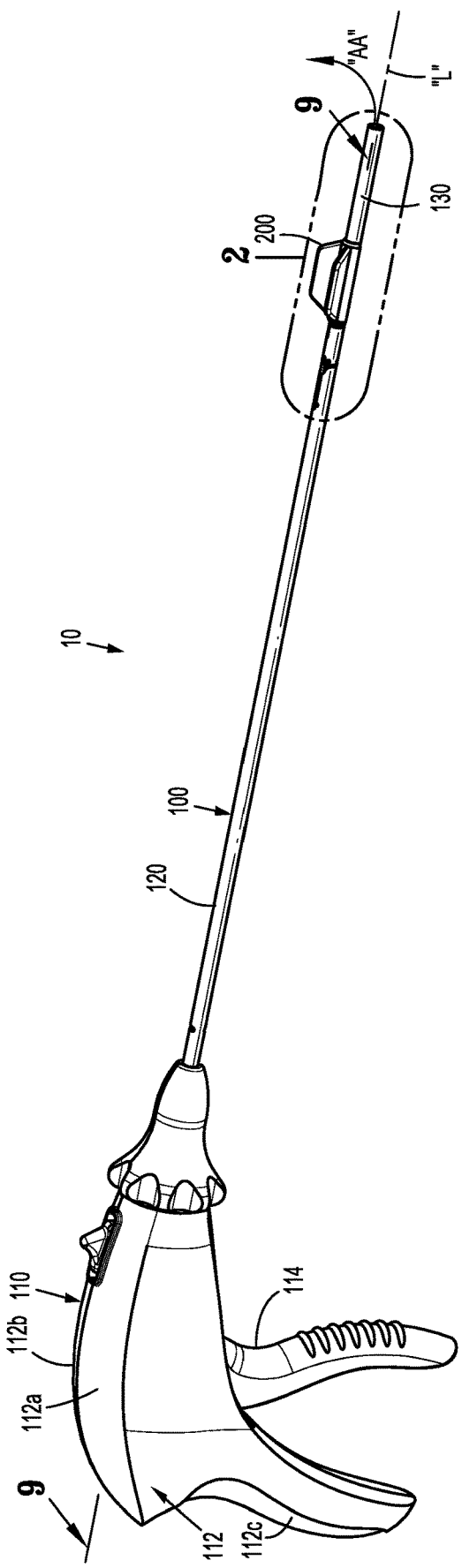
FIG. 1 is a perspective view of an endoscopic surgical system in accordance with the present disclosure.

Embodiments of the presently disclosed devices are described in detail with reference to the drawings, in which like reference numerals designate identical or corresponding elements in each of the several views. As used herein, the term "distal" refers to that portion of the device that is farther from the user, while the term "proximal" refers to that portion of the device that is closer to the user.

Non-limiting examples of endoscopic surgical devices according to the present disclosure include manual, mechanical and/or electromechanical surgical tack appliers (i.e., tackers) and the like. For a more detailed description of similar endoscopic surgical devices and components thereof that can be used with, or adapted for use with, the presently described endoscopic surgical devices, reference can be made to U.S. patent application Ser. No. 13/974,338, filed on Aug. 23, 2013 and entitled "Articulating Apparatus for Endoscopic Procedures," the entire contents of which are hereby incorporated by reference herein.

Referring initially to FIGS. 1-8, an endoscopic surgical system is shown generally as 10. Endoscopic surgical system 10 includes an endoscopic surgical device in the form of an endoscopic surgical tack applier or tacker 100, and a shipping wedge 200. Tack applier 100 includes a handle assembly 110 and an elongated body portion 120 extending distally along a longitudinal axis "L" from handle assembly 110 to an end effector 130 at a distal end thereof that is selectively detachable/attachable from/to elongated body portion 120.

Handle assembly 110 includes a handle housing 112 having a first half-section 112a and a second half section 112b joined to one another to form a stationary handle 112c. First half-section 112a and second half section 112b of handle housing 112 may be joined to one another using known methods by those of skill in the art, including and not limited to welding, fasteners (i.e., screws) and the like.

Figures 9, 10:
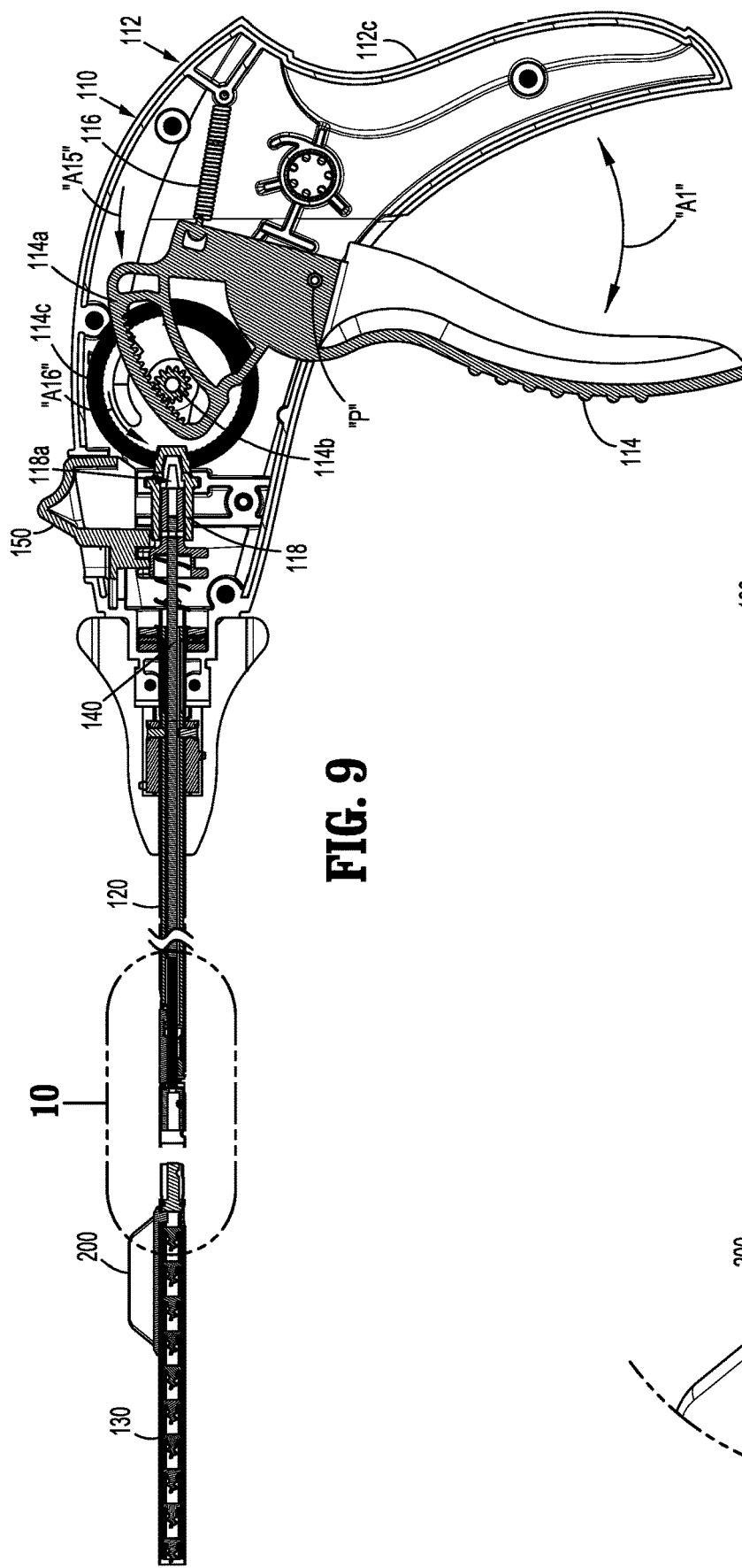
FIG. 9 is a cross-sectional view of the endoscopic surgical system of FIG. 1, as taken along line segment 9-9 of FIG. 1, the endoscopic surgical system shown in a first state.
FIG. 10 is an enlarged, elevational view of the indicated area of detail shown in FIG. 9.
Figure 13:
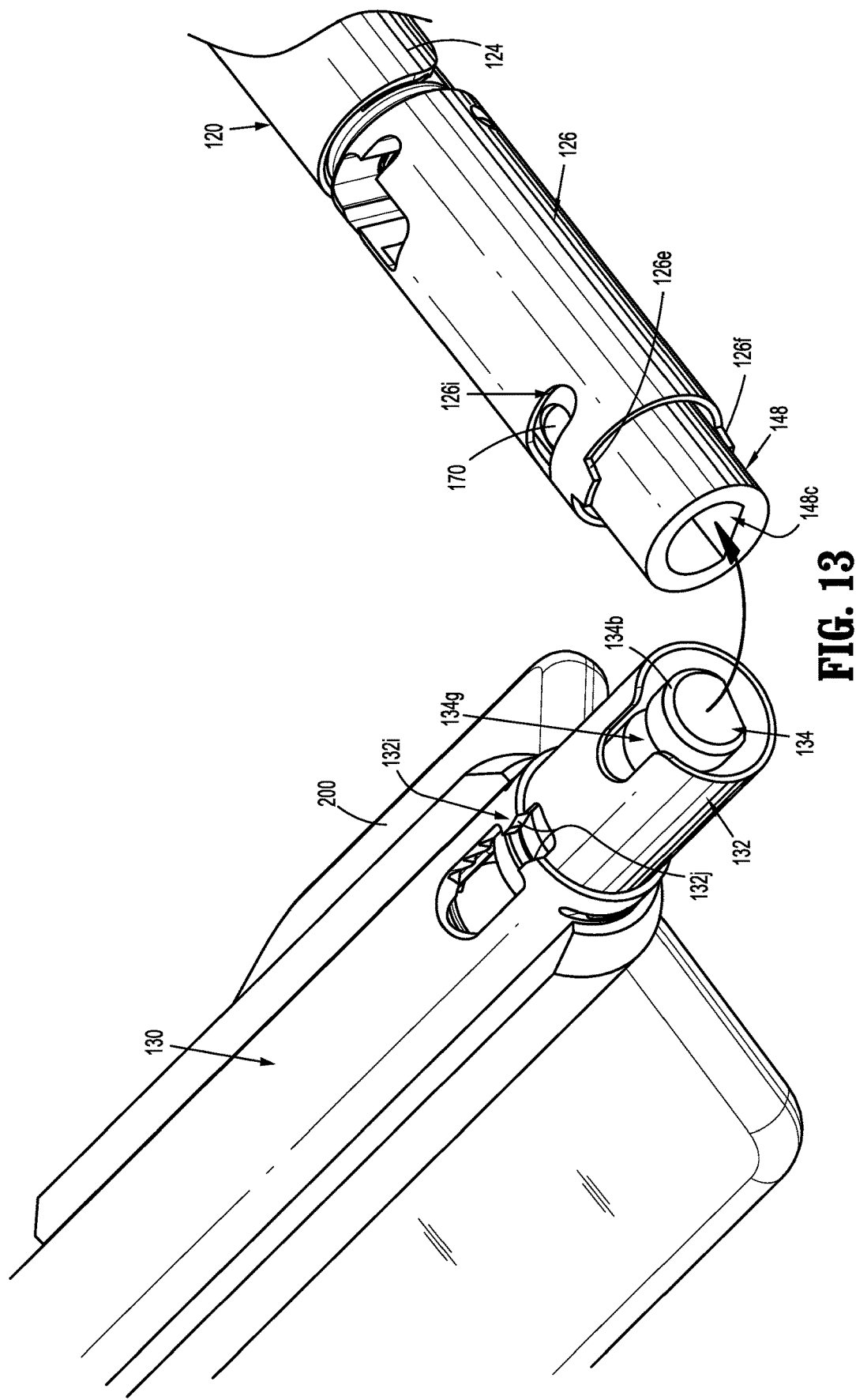

Referring also to FIG. 9, handle assembly 110 includes a trigger 114 connected to handle housing 112 about a pivot point "P" for pivoting movement relative to handle housing 112 as illustrated by arrow "A1." Handle assembly 110 includes a biasing member 116 configured for maintaining trigger 114 in an extended or un-actuated position. Biasing member 116 is also configured to have a spring constant sufficient to return trigger 114 to the un-actuated position.

Trigger 114 defines a gear rack 114a formed thereon at a location opposite a hand grip portion and remote from the pivot point "P" of trigger 114. Gear rack 114a of trigger 114 is configured for operative engagement with a pinion gear 114b rotatably supported in handle housing 112.

Handle assembly 110 further includes a bevel gear 114c, in the form of a crown gear, operatively engaged/associated with pinion gear 114b and rotatably mounted to handle housing 112. Bevel gear 114c is operatively engaged/associated with a drive gear 118 rotatably mounted to handle housing 112. Gear components such as gear rack 114a, pinion gear 114b, bevel gear 114c, drive gear 118, and/or teeth thereof can have any suitable configuration for interacting/enmeshing with one another. For example, these gear components can be configured and dimensioned such that one complete squeeze of trigger 114 results in one complete revolution of pinion gear 114b causing drive gear 118 to rotate the required number of turns to deliver the surgical fastener.

As seen in FIGS. 9 and 11, drive gear 118 defines a non-circular opening 118a dimensioned to receive a proximal end portion of an inner shaft assembly 140 of elongated body portion 120. Non-circular opening 118a can have a transverse cross-sectional profile with any suitable shape such as a D-shape, for example, to transmit torque to the inner shaft assembly 140.

Referring also to FIGS. 10 and 11, elongated body portion 120 includes an outer tube 122 that supports inner shaft assembly 140. Outer tube 122 includes a proximal portion 124 and a distal portion 126.

Figure 7:
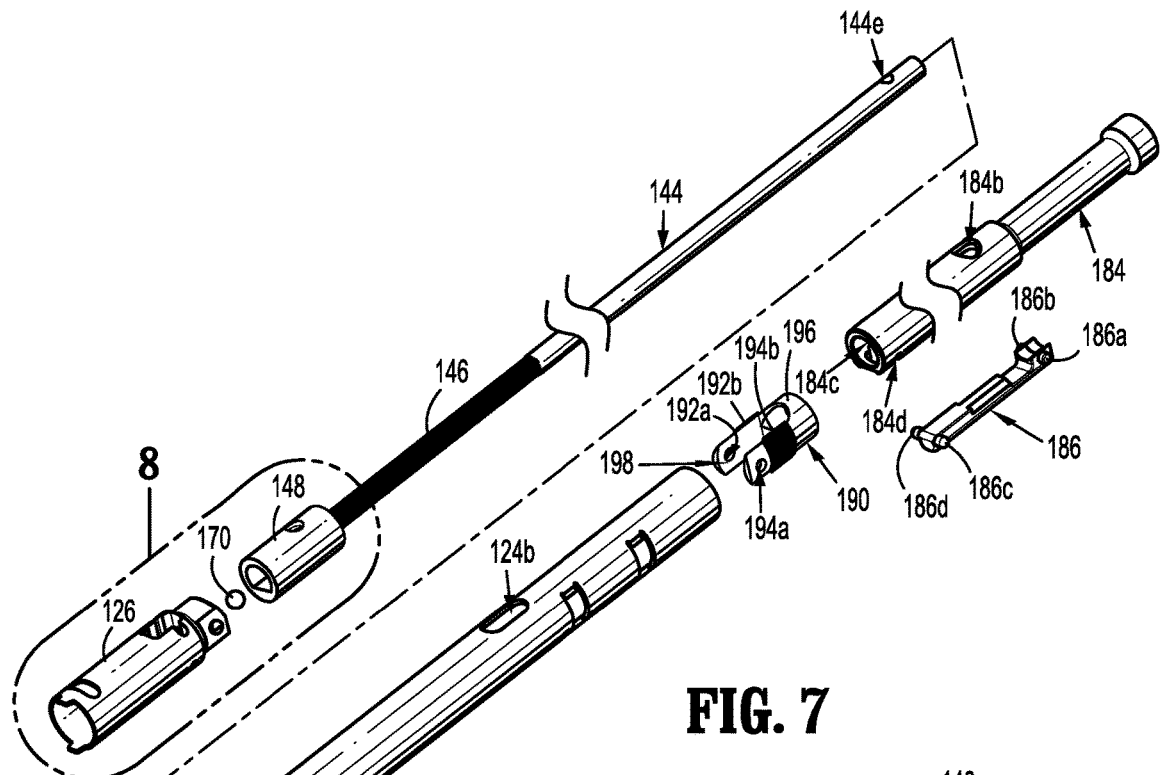
FIG. 7 is a perspective view, with parts separated, of an elongated body portion of the endoscopic surgical system of FIG. 1.

With reference to FIG. 7, proximal portion 124 includes an outer surface 124a that defines a throughbore 124b extending transversely therethrough and an inner surface 124c that defines lumen 124d extending longitudinally therealong. A distal end of inner surface 124c defines a threaded portion 124e therealong.

Figure 8:
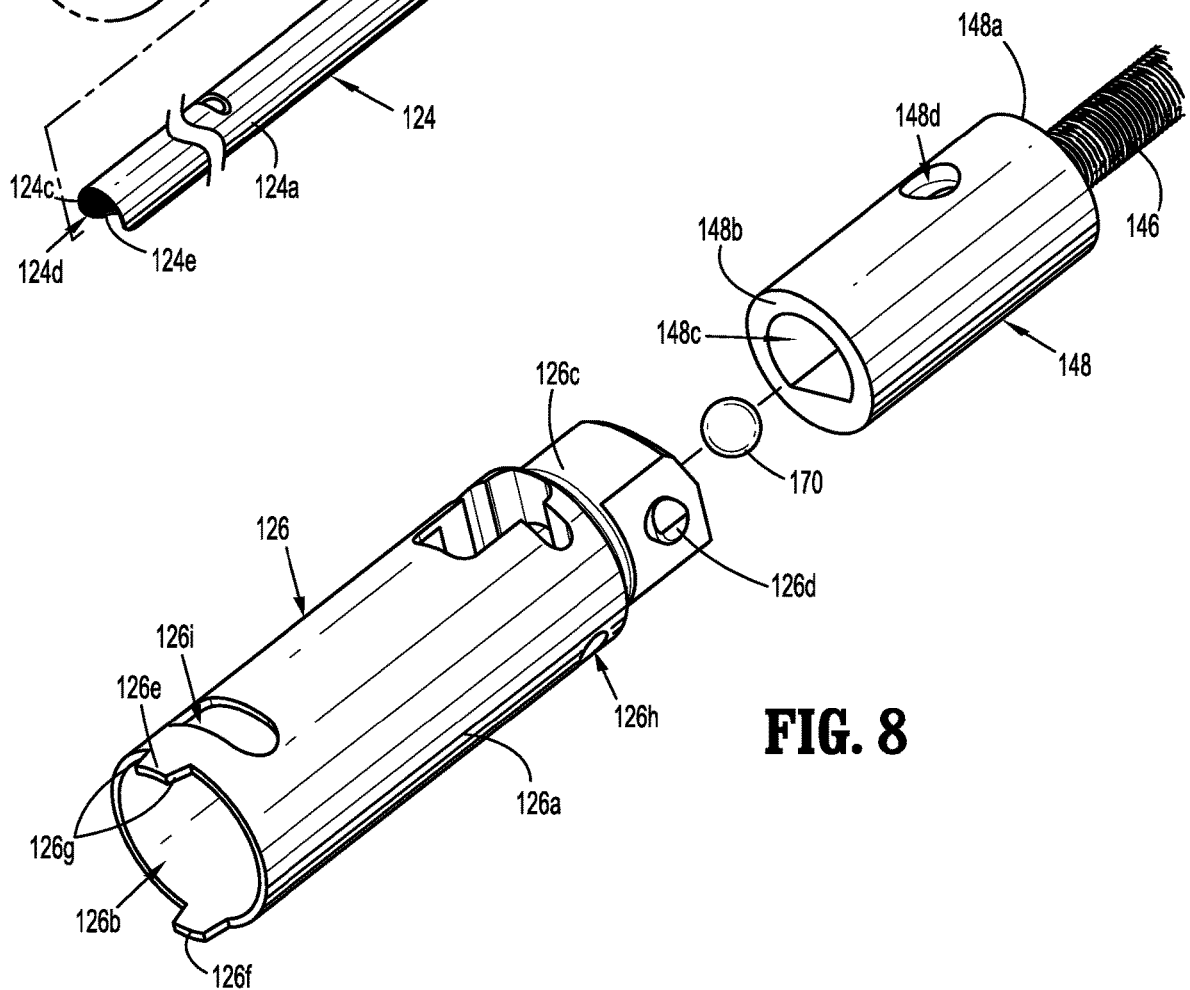
FIG. 8 is an enlarged, perspective view of the indicated area of detail shown in FIG. 7.

Referring to FIG. 8, distal portion 126 of outer tube 122 includes an outer wall 126a. An inner surface of outer wall 126a defines a central bore 126b. A pivot portion 126c extends proximally from outer wall 126a and includes a pair of opposed protuberances 126d, each of which extends from one of the side surfaces of pivot portion 126c (only one of the pair of opposed protuberances 126d shown in FIG. 8). Outer wall 126a extends distally to first and second rotational lock features 126e (e.g., on bottom of outer tube 122—shown facing upwards in FIG. 8), 126f (e.g., on top of outer tube 122—shown facing downwards in FIG. 8). Each of first and second rotational lock features 126e, 126f includes a pair of tapered side surfaces 126g. One or both of first and second rotational lock features 126e, 126f can have any suitable shape such as trapezoidal, for example, to facilitate rotational locking interaction with a counterpart shape as described in greater detail below. Outer wall 126a further defines a pair of opposed proximal apertures 126h and an elongated, transverse distal slot 126i, each of which extends through outer wall 126a. As seen in FIGS. 14 and 15, distal portion 126 includes an alignment feature 126j positioned thereon to facilitate alignment of distal portion 126 relative to end effector 130, as described in greater detail below.

Referring again to FIG. 11, inner shaft assembly 140 includes a coupling member 142 at a proximal end thereof that is slidably supported within non-circular opening 118a of drive gear 118 and rotatable therewith as illustrated by arrows "A2" and "A3." Coupling member 142 includes a stem 142a having a non-circular, transverse, cross-sectional outer profile at a proximal end thereof that is configured and dimensioned to correspond to non-circular opening 118a of drive gear 118, thereby providing slidable movement therein relative to drive gear 118. In some embodiments, non-circular stem 142a has a D-shape transverse cross-sectional outer profile. Coupling member 142 extends distally to a mounting portion 142b, operatively engaged/associated with a slider 150, and a biasing member 160. Mounting portion 142b defines a bore 142c that receives a proximal end of biasing member 160 and includes a plurality of annular flanges 142d that extends therefrom. The proximal end of biasing member 160 is secured to an inner surface of mounting portion 142b using any known technique such as peening, welding, fastening or the like. Non-circular stem 142a defines a passage 142d in communication with bore 142c of mounting portion 142b. Non-circular stem 142a includes a transverse passage 142e therethrough in communication with passage 142d.

Inner shaft assembly 140 includes a proximal rigid portion 144 having a proximal end 144a received within passage 142d of coupling member 142. Proximal rigid portion 144 defines an aperture 144e (FIG. 7) therethrough in communication with transverse passage 142e of coupling member 142. Aperture 144e of proximal rigid portion 144 and transverse passage 142e of coupling member 142 receive a fastener or a pin (not shown) therein to secure proximal rigid portion 144 within passage 142d of coupling member 142. In some embodiments, proximal end 144a of proximal rigid portion 144 is secured within passage 142d of coupling member 142 using any known technique such as peening, welding, fastening or the like. Proximal rigid portion 144 extends to a distal end 144b connected to a proximal end 146a of a distal flexible portion 146 of inner shaft assembly 140.

With reference to FIGS. 8 and 12, a distal end 146b of distal flexible portion 146 is connected to a proximal end 148a of a distal tube 148. Distal tube 148 extends to a distal end 148b and defines a longitudinal bore 148c that opens through distal end 148b thereof. Distal tube 148 also defines an opening 148d therethrough that is transverse to, and in communication with, longitudinal bore 148c. Longitudinal bore 148c has a D-shaped transverse cross-sectional profile. Longitudinal bore 148c may have any suitable non-circular shape and/or dimension for receiving/interacting with one or more components of end effector 130. Opening 148d of distal tube 140 is configured to receive a detent 170 therein. Detent 170 may have any suitable shape and/or dimension such as spherical and/or rounded for example. In some embodiments, detent 170 may be a ball.

As seen in FIG. 11, a slider 150 is slidably supported on handle assembly 110 and includes a finger pad 152 extending from an outer surface of handle assembly 110. Slider 150 further includes a mating portion 154 having a flange 156 engaged with annular flanges 142d of coupling member 142. Slider 150 is biased to a proximal position by axial forces generated by biasing member 160. The axial forces are transmitted through interaction between flange 156 of slider 150 and annular flanges 142d of coupling member 142. Slider 150 is selectively movable to a distal position to axially advance inner shaft assembly 140 relative to longitudinal axis "L," as described in greater detail below.

Referring again to FIG. 11, an articulation assembly 180 includes an articulation actuator 180a supported at a proximal end of elongated body portion 120 and rotatable thereabout as illustrated by arrow "A4." Articulation actuator 180a is axially fixed within a recess 111 defined within handle assembly 110 via one or more flanges 111a. In some embodiments, flange 111a has an annular configuration. Articulation assembly 180 includes a drive assembly 180b. Drive assembly 180b includes a tubular sleeve 182, a slidable tube 184, and an articulation arm 186.

Tubular sleeve 182 of drive assembly 180b includes first and second protubuerances 182a, 182b extending therefrom that are slidably received by a helical channel 181 defined within articulation actuator 180a so that rotation of articulation actuator 180a about outer tube 122 of elongated body portion 120 enables tubular sleeve 182 to axially slide relative to articulation actuator 180 and outer tube 122 as described in greater detail below. Tubular sleeve 182 further includes first and second pins 182c, 182d that are received within, and slidable along, opposite ends of throughbore 124b of outer tube 122, respectively.

Slidable tube 184 of drive assembly 180b is supported within outer tube 122 and slidable therealong. Slidable tube 184 defines first and second apertures 184a, 184b that are dimensioned to receive ends of first and second pins 182c, 182d of tubular sleeve 182 depending respectively therefrom. First and second pins 182c, 182d may be secured within first and second apertures 184a, 184b using any known technique such as welding, friction fit, snap fit or the like. First and second apertures 184a, 184b are disposed in communication with throughbore 124b and longitudinally movable therealong as tubular sleeve 182 axially translates relative to the longitudinal axis "L."

With reference to FIG. 7, slidable tube 184 further defines a longitudinally extending lumen 184c therethrough and an articulation member recess 184d that is transverse to lumen 184c and in communication therewith.

Articulation arm 186 of drive assembly 180b includes first and second protuberances 186a, 186b that extend from side surfaces of a proximal end thereof and third and fourth protuberances 186c, 186d that extend from side surfaces of a distal end thereof. First and second protuberances 186a, 186b are received within articulation member recess 184d of slidable tube 184 and each of third and fourth protuberances 186c, 186d are received within one of the pair of opposed apertures 126h of distal portion 126 of outer tube 122, respectively (see FIG. 8).

With continued reference to FIG. 7, a clevis 190 of articulation assembly 180 includes first and second arms 192, 194 that are coupled by a base 196 and that extend distally from base 196. Clevis 190 defines a central passage 198 therethrough. First and second arms 192, 194 define respective apertures 192a, 194a transversely therethrough and include respective threaded surfaces 192b, 194b thereon. Apertures 192a, 194a of first and second arms 192, 194 receive the pair of opposed protuberances 126d of distal portion 126 of outer tube 122 and base 196 is supported on a distal end of slidable tube 184 with the distal end of slidable tube 184 received within central passage 198 of clevis 190. With articulation arm 186 supporting clevis 190 between slidable tube 184 and distal portion 126 of outer tube 122 via protuberances 186a-186d, and with the pair of opposed protuberances 126d of distal portion 126 of outer tube 122 received within apertures 192a, 194a of clevis 190, distal portion 126 of outer tube 122 is pivotally coupled to clevis 190. Threaded surfaces 192b, 194b of clevis 190 are threadably engaged with threaded surface 124e of proximal portion 124 of outer tube 122.

Optionally, clevis 190 can be rotated relative to proximal portion 124 of outer tube 122 in order to adjust a longitudinal position of distal portion 126 of outer tube 122 relative to proximal portion 124 to account for changes in length of distal flexible portion 146 of inner shaft assembly 140.

Turning back to FIG. 4, end effector 130 is configured to removably receive a shipping wedge 200 and for selective connection to elongated body portion 120. End effector 130 includes an outer housing 132 coupled to an inner housing 134 by a spring clip 136. End effector 130 supports and stores a plurality of surgical fasteners or anchors 138 such that handle assembly 110, elongated body portion 120, and end effector 130 cooperate to selectively release or fire one or more of the plurality of anchors 138 from end effector 130, as described in greater detail below.

Outer housing 132 includes an outer surface 132a and a threaded inner surface 132b that defines a lumen 132c longitudinally therethrough. With reference to FIG. 5, outer housing 132 includes a proximal segment 132d and a distal segment 132e. Proximal and distal segments 132d, 132e of outer housing 132 have different diameters and are separated at a ledge or shoulder 132f. Distal segment 132e of outer housing 132 defines a pair of side slots 132g (only one of the pair of side slots 132g being shown in FIG. 5) in an outer surface thereof. Outer housing 132 defines a transverse aperture 132h through outer surface 132a and includes a pair of rotational lock features 132i (only one of the pair of rotational lock features 132i being shown in FIG. 5) that receives first and second rotational lock features 126e, 126f of distal portion 126 of outer tube 122. Each of the pair of rotational lock features 132i includes a pair of engaging surfaces 132j. One or both of the pair of engaging surfaces 132j may include one or more angled, tapered, and/or curved surfaces. Transverse aperture 132h extends along portions of both proximal and distal segments 132d, 132e of outer housing 132. As seen in FIGS. 14 and 15, proximal segment 132d of outer housing 132 includes an alignment feature 132k positioned to align with alignment feature 126j of distal portion 126 of outer tube 122. Although shown as ribs, alignment features 126j, 132k can include structure or indicia of any size, shape, and/or color suitable for orienting end effector 130 relative to elongated body portion 120 to facilitate proper connection therebetween.

With continued reference to FIG. 4, inner housing 134 includes a support body 134a having a drive shaft 134b extending proximally therefrom and first and second tines 134c, 134d extending distally therefrom. First and second tines 134c, 134d are disposed in spaced-apart relation to one another and define an anchor channel 134e therebetween that is configured and dimensioned to receive the plurality of anchors 138. Support body 134a defines an annular channel 134f radially therearound that aligns with the pair of side slots 132g of outer housing 132 for receiving clip 136 to longitudinally fix inner housing 134 relative to outer housing 132. Drive shaft 134b defines an annular recess 134g that extends around an arcuate surface 134h of drive shaft 134b. Drive shaft 134b further includes a flat surface 134j disposed opposite to arcuate surface 134h.

With reference to FIGS. 4-8, shipping wedge 200 includes a body portion 202, and first and second wings 204, 206 that extend from body portion 202. Body portion 202 has an outer surface 202a and an inner surface 202b. Inner surface 202b defines a channel 202c that extends axially along body 202. Channel 202c is configured and dimensioned to receive outer housing 132 of end effector 130. An engagement nub 208 extends from inner surface 202b into channel 202c of shipping wedge 200. Engagement nub 208 is receivable within transverse aperture 132h of outer housing 132 and within a proximal portion of anchor channel 134e while shipping wedge 200 is secured to end effector 130. First and second wings 202, 204 are biased by body portion 202 in an initial state in which first and second wings 202, 204 are disposed in spaced-apart relation and in which channel 202c is configured and dimensioned to engage outer housing 132 of end effector 130 for maintaining shipping wedge 200 secured to end effector 130. First and second wings 202, 204 are configured and dimensioned to flex toward one another to flex body portion 202 outwardly and to further open channel 202c for facilitating attachment and/or removal of shipping wedge 200 to/from end effector 130 (see FIG. 20).

With reference to FIGS. 9-22, a loading of end effector 130 to handle assembly 110, and an operation of tacker 100 is described. As shown in FIGS. 9-12, the proximal end of end effector 130 is aligned with the distal end of elongated body portion 120. As indicated by arrow "A5," slider 150 is advanced from an initial position shown in FIG. 9 to the distal position shown in FIG. 11. Flange 156 of slider 150 axially drives annular flanges 142d of coupling member 142 to axially advance coupling member 142 such that non-circular stem 142a thereof slides within and relative to non-circular opening 118a of drive gear 118, as indicated by arrow "A2" (FIG. 11). With proximal rigid portion 144 of inner shaft assembly 140 fixedly secured to coupling member 142, axial movement of coupling member 142 drives proximal rigid portion 144 of inner shaft assembly 140 axially such that distal flexible portion 146 drives distal tube 148 distally, as indicated by arrows "A6," as seen in FIG. 12. As the distal end of distal tube 148 advances distally beyond the distal end of distal portion 126 of outer tube 122, detent 170, while positioned within opening 148d of distal tube 148, slides/floats distally along the inner surface of outer wall 126a of distal portion 126. Once elongated slot 126i of distal portion 126 and opening 148d of distal tube 148 are longitudinally aligned, detent 170 is free to float within into opening 148d of distal tube 148 and within slot 126i of distal portion 126 (see arrow "A7") in order to enable receipt of inner housing 134 within bore 148c of distal tube 148.

As seen in FIGS. 14-16, with alignment features 132k, 126j aligned with one another, drive shaft 134b of inner housing 134 is then advanced into longitudinal bore 148c of distal tube 148 as indicated by arrows "A8" and "A9." Drive shaft 134b is positioned such that annular recess 134g of drive shaft 134b is aligned with detent 170 and in communication with opening 148d of distal tube 148.

With inner housing 134 inserted into bore 148c of distal tube 148, and with annular recess 134g of drive shaft 134b in registration with detent 170, slider 150 is moved in a proximal direction to withdraw or move distal tube 148 in a proximal direction to urge detent 170 out of elongated slot 126i and into annular recess 134g of drive shaft 134b and opening 148d of distal tube 148.

Figure 18:
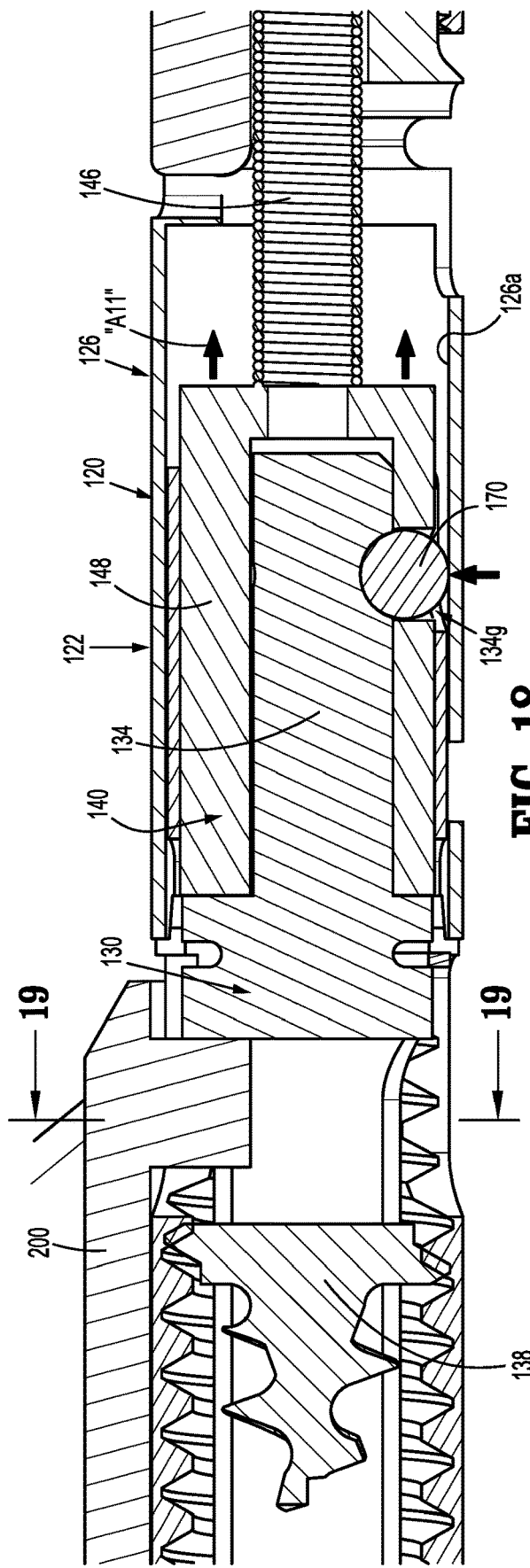

With reference to FIGS. 17 and 18, drive shaft 134b of end effector 130 is then further proximally advanced into distal tube 148 as indicated by arrows "A11" such that detent 170 proximally slides/floats along inner surface of outer wall 126a of distal portion 126 until inner shaft assembly 140 and slider 150 are positioned back into their initial positions (see FIG. 9) and end effector 130 and elongated body portion 120 are fully engaged and locked together via detent 170.

Figure 19:
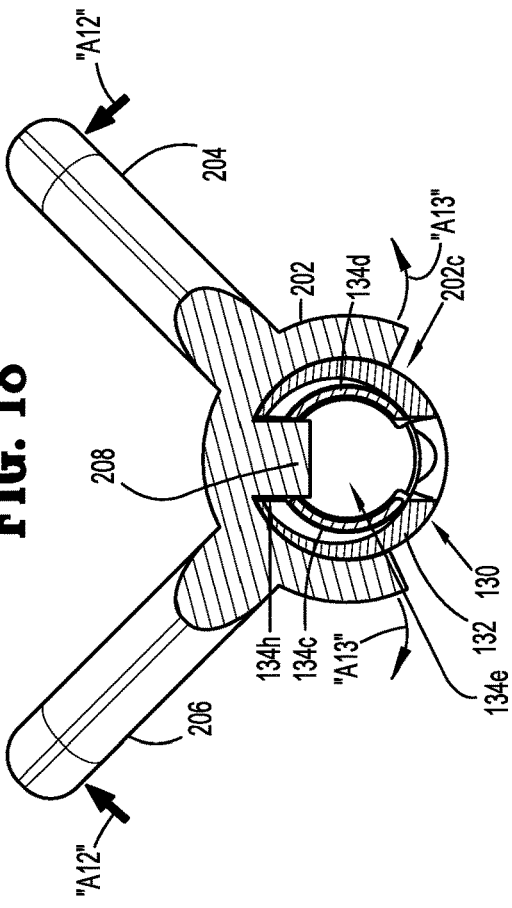
FIGS. 19-22 are progressive views illustrating a removal of the shipping wedge from the endoscopic surgical system of FIG. 1.
Figure 22:
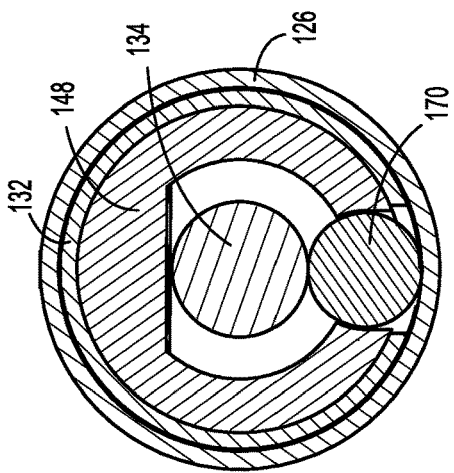
Figure 20:
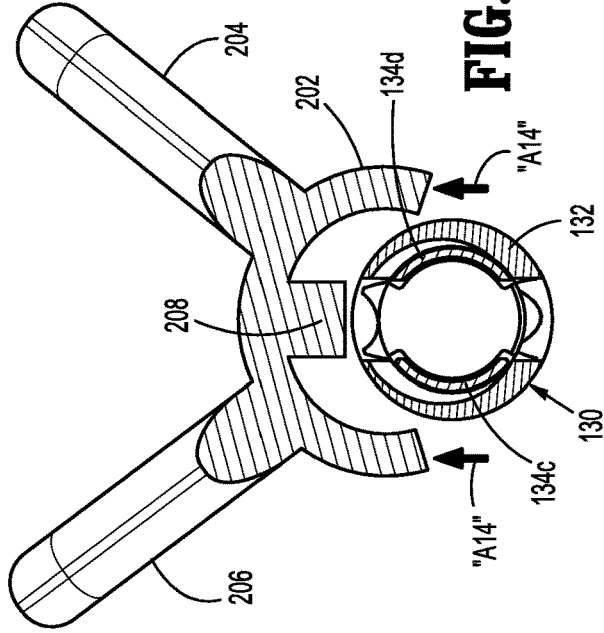
Figure 21:
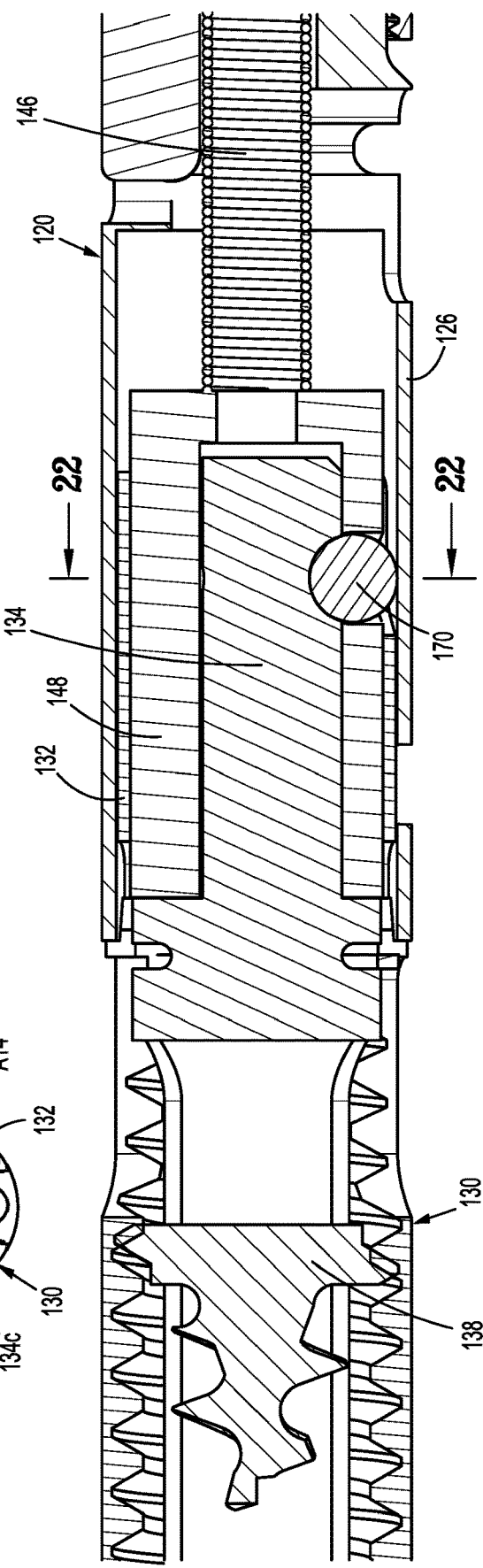

As seen in FIGS. 19 and 20, to remove shipping wedge 200, first and second wings 204, 206 are approximated or flexed toward one another so that body portion 202 flexes radially outwardly as indicated by arrows "A12" and "A13," respectively. Shipping wedge 200 may then be separated from end effector 130 as indicated by arrows "A14." With shipping wedge 200 removed, as shown in FIGS. 21 and 22, tacker 100 can be fired as described in greater detail below.

During use, a clinician may desire to articulate end effector 130 relative to elongated body portion 120 and longitudinal axis "L" as indicated by arrow "AA," shown in FIG. 1. To effectuate articulation, articulation actuator 180a of articulation assembly 180 is rotated as indicated by arrow "A4." Rotation of articulation actuator 180a imparts linear movement to tubular sleeve 182 as illustrated by arrow "A17," as shown in FIG. 11. Axial movement of tubular sleeve 182 enables first and second pins 182c, 182d to axially slide slidable tube 184 within outer tube 122 relative thereto. As slidable tube 184 is drawn proximally, articulation arm 186 articulates distal portion 126 of outer tube 122 relative to proximal portion 124 of outer tube in the direction illustrated by arrow "AA." Rotation of articulation actuator 180a in an opposite direction drives slidable tube 184 distally and articulates distal portion 126 of outer tube 122 back toward its initial position in axial alignment with proximal portion 124 of outer tube 122.

To fire one or more of the plurality of anchors 138, trigger 114 is drawn proximally toward stationary handle 112c as indicated by arrow "A1," as shown in FIG. 9. While trigger 114 pivots about pivot point "P," radially movement imparted by gear rack 114a, indicated by arrow "A15," rotates pinion gear 114b and bevel gear 114c as indicated by arrow "A16." With drive gear 118 and coupling member 142 coupled together by non-circular profiles of noncircular opening 118a of drive gear 118 and non-circular stem 142a of coupling member 142, as shown in FIG. 11, rotation of bevel gear 114c imparts rotation on drive gear 118 and coupling member 142 of inner shaft assembly 140, as indicated by arrow "A3." While distal tube 148 of inner shaft assembly 140 rotates, drive shaft 134b of inner housing 134 rotates such that first and second tines 134c, 134d rotate the plurality of anchors 138 distally along threaded inner surface 132b of outer housing 132. With outer housing 132 rotationally fixed relative to outer tube 122 via engagement of first and second rotational lock features 126e, 126f with the pair of rotational lock features 132i (FIG. 5), a distal-most anchor of the plurality of anchors 138 is dispensed from distal end of end effector 130 upon approximation of trigger 114 and stationary handle 112c. Trigger 114 is then released and unapproximated from stationary handle 112c to its initial position relative to handle 112c. The firing process can be repeated as desired until each of the plurality of anchors 138 is dispensed from end effector 130.

To remove end effector 130 from elongated body portion 120, for example, after a plurality or all of anchors 138 are dispensed from end effector 130, slider 150 is again advanced distally until detent 170 is in registration with or positioned within elongated slot 126i of outer tube 122. Once detent 170 is received in elongated slot 126i, end effector 130 may be separated from elongated body portion 120 and a new or reloaded end effector 130 may be reattached and reused, as described above.

As can be appreciated, securement of any of the components of the presently disclosed devices can be effectuated using known fastening techniques such welding, crimping, gluing, fastening, etc.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. A surgical device comprising:
an elongated body portion including an outer tube and an inner shaft assembly, the inner shaft assembly having a distal tube defining a non-circular bore in a distal end thereof, the inner shaft assembly being longitudinally movable through the outer tube, the outer tube and the distal tube defining corresponding openings extending transversely therethrough;
an end effector configured and dimensioned for selective connection to the elongated body portion, the end effector supporting surgical fasteners positioned to distally advance through the end effector, the end effector including a drive shaft extending proximally therefrom and defining an annular recess in an outer surface thereof, the drive shaft having a non-circular transverse cross-sectional profile that is complimentary in shape to the non-circular bore of the distal tube; and
a detent movable within the openings of the elongated body portion, the detent positionable between the annular recess of the drive shaft and the outer tube of the elongated body portion to connect the end effector to the elongated body portion in response to insertion of the drive shaft into the non-circular bore of the distal tube.

2. The surgical device of claim 1, wherein the annular recess of the drive shaft has an arcuate cross-sectional profile.

3. The surgical device of claim 2, wherein the annular recess of the drive shaft partially circumscribes the drive shaft.

4. The surgical device of claim 1, wherein the inner shaft assembly includes a proximal rigid portion connected to a distal flexible portion.

5. The surgical device of claim 1, wherein the drive shaft of the end effector and the bore of the distal tube have complementary D-shaped cross-sectional profiles.

6. The surgical device of claim 1, wherein the drive shaft of the end effector rotates in response to rotation of the inner shaft assembly.

7. The surgical device of claim 1, wherein the end effector includes an outer housing positioned about the drive shaft, the outer housing of the end effector and the outer tube of the elongated body portion including corresponding mating structures configured and dimensioned for engagement to rotationally align and lock together the elongated body portion and the end effector.

8. The surgical device of claim 1, further including an articulation assembly having an articulation actuator supported at a proximal end of the elongated body portion and a drive assembly, the outer tube of the elongated body portion including a proximal portion and a distal portion, the drive assembly operatively coupled between the articulation actuator and the distal portion of the outer tube, the articulation actuator being actuatable to articulate the distal portion of the outer tube relative to the proximal portion of the outer tube for articulating the end effector relative to a longitudinal axis defined through the elongated body portion.

9. The surgical device of claim 8, wherein the drive assembly includes a slidable tube and an articulation arm, the articulation arm pivotally coupled to the slidable tube and the distal portion of the outer tube, the articulation actuator coupled to the slidable tube, wherein rotation of the articulation actuator longitudinal translates the slidable tube through elongated body portion, wherein longitudinal translation of the slidable tube longitudinally translates the articulation arm to enable the end effector to articulate relative to the longitudinal axis.

10. The surgical device of claim 1, wherein the detent is configured and dimensioned to float between the end effector and the elongated body portion to enable selective connection between the end effector and the elongated body portion.

11. The surgical device of claim 10, wherein the detent has a spherical shape.

12. An end effector configured and dimensioned for releasable connection to an elongated body portion of a surgical fastener applying device, the elongated body portion including a detent, the end effector comprising:
a plurality of surgical fasteners distally advanceable through the end effector; and
a proximally extending drive shaft configured and dimensioned for insertion into the elongated body portion of the surgical fastener applying device, the drive shaft defining an annular recess configured and dimensioned to receive the detent such that the detent is positionable between the annular recess and the elongated body portion of the surgical fastener applying device to connect the end effector to the surgical fastener applying device.

13. The end effector of claim 12, wherein the annular recess of the drive shaft defines an arcuate cross-sectional profile.

14. The end effector of claim 12, wherein the annular recess of the drive shaft partially circumscribes the drive shaft.

15. The end effector of claim 12, wherein the drive shaft has a non-circular transverse cross-sectional profile.

16. The end effector of claim 12, wherein the drive shaft is D-shaped.

17. The end effector of claim 12, further including an outer tube supporting the proximally extending drive shaft, the drive shaft being rotatable to fire the plurality of fasteners, which are supported within the outer tube from the outer tube.

18. A surgical fastener applying device configured and dimensioned for releasable connection to an end effector, the surgical fastener applying device comprising:
an elongated body portion including an outer tube and an inner shaft assembly, the inner shaft assembly having a distal tube defining a non-circular bore in a distal end thereof, the inner shaft assembly being longitudinally movable through the outer tube, the outer tube and the distal tube defining corresponding openings extending transversely therethrough, the inner shaft assembly being actuatable to distally advance at least one surgical fastener through the end effector; and
a detent movable within the openings of the elongated body portion, the detent configured and dimensioned to float between the end effector and the elongated body portion to enable selective connection between the end effector and the elongated body portion.

19. The surgical fastener applying device of claim 18, wherein the detent has a spherical shape.

20. The surgical fastener applying device of claim 18, further including an articulation assembly having an articulation actuator supported at a proximal end of the elongated body portion and a drive assembly, the outer tube of the elongated body portion including a proximal portion and a distal portion, the drive assembly operatively coupled between the articulation actuator and the distal portion of the outer tube, the articulation actuator being actuatable to articulate the distal portion of the outer tube relative to the proximal portion of the outer tube for articulating the end effector relative to a longitudinal axis defined through the elongated body portion.

* * * * *